(12) United States Patent
Binkowski

(10) Patent No.: US 7,836,852 B2
(45) Date of Patent: Nov. 23, 2010

(54) METHODS FOR MANIPULATING FISH SPAWNING CYCLES

(75) Inventor: Frederick P. Binkowski, Sheboygan, WI (US)

(73) Assignee: UWM Research Foundation, Inc., Milwaukee, WI (US)

( * ) Notice: Subject to any disclaimer, the term of this patent is extended or adjusted under 35 U.S.C. 154(b) by 13 days.

(21) Appl. No.: 11/951,882

(22) Filed: Dec. 6, 2007

(65) Prior Publication Data

US 2008/0134983 A1    Jun. 12, 2008

Related U.S. Application Data

(60) Provisional application No. 60/873,783, filed on Dec. 8, 2006.

(51) Int. Cl.
*A01K 63/00* (2006.01)
(52) U.S. Cl. ................. 119/247; 119/215; 119/217
(58) Field of Classification Search .............. 119/300, 119/200, 215, 217
See application file for complete search history.

(56) References Cited

PUBLICATIONS

RC Heidinger, TB Kayes—Culture of Nonsalmonid Freshwater Fishes, 1993—books.google.com.*
D Merriman, HP Schedl—Journel of Experimental Zoology, 1941—interscience.wiley.com.*
Developing Domesticated Yellow Perch Broodstock, Principle Investigator Frederick P. Binkowski, Senior Scientist, University of Wisconsin, Milwaukee, Great lakes WATER Institute, Submitted to Bell Aquaculture, LLC., Albany, Indiana, Jan. 8, 2007.
Gall, G.A.E., Aquacultural Genetics and Breeding, National Research Priorities, vol. I, Committee on Aquacultural Genetics and Breeding, United States Department of Agriculture, Cooperative State Research Service, Mar. 1988.
Gall, G.A.E., Aquacultural Genetics and Breeding, National Research Priorities, vol. II, Committee on Aquacultural Genetics and Breeding, United States Department of Agriculture, Cooperative State Research Service, Mar. 1988.
Behm, D., "Thousands of Baby Fish Released in Milwaukee River," Milwaukee Journal Sentinel, May 13, 2003.
Bentsen, H.B. et al., "Genetic Improvement of Farmed Tilapias: Growth Performance in a Complete Diallel Cross Experiment with Eight Strains of *Oreochromis niloticus*", Aquaculture 160, Elsevier, pp. 145-173, 1998.

(Continued)

*Primary Examiner*—Timothy D Collins
*Assistant Examiner*—Justin Benedik
(74) *Attorney, Agent, or Firm*—Michael Best & Friedrich LLP

(57) ABSTRACT

A method of manipulating a spawning cycle of perch across multiple generations that includes identifying a desired out-of-cycle spawning period for perch, selecting a geographic strain of perch having a natural spawning period in proximity to the desired out-of-cycle spawning period, developing a first generation broodstock from the geographic strain, where the broodstock's natural spawning period has been shifted to the desired spawning period using at least one of temperature and photoperiod manipulation, identifying a second desired out-of-cycle spawning period, developing a second generation broodstock from the first generation broodstock, where the second generation broodstock's spawning period has been shifted from the desired out-of-cycle spawning period to the second desired out-of-cycle spawning period using at least one of temperature and photoperiod manipulation. Exemplary strains include strains from the East Coast of the United States, including strains from the Chesapeake Bay, the Sassafras River, and the Choptank River.

18 Claims, 3 Drawing Sheets

OTHER PUBLICATIONS

Binder, D., "Biologists Breathe New Life into Sturgeon'Ancient Habit," The New York Times, Jul. 2, 2002.

Brinkowski, F.P., "Intensive Aquaculture Technology (IAT) for Yellow Perch: the Cookbook Version", Public Presentation, Given at Indiana Aquaculture Association Spring Meeting & Workshop, Monticello, Indiana, Mar. 18, 2006; Michigan Aquaculture Business Conference "Sustainable Aquaculture", Lansing, MI, Feb. 10, 2006; and Yellow Perch Workshop of the Joint Meeting of the Nebraska Aquaculture Association and The Sandhills Yellow Perch Cooperative, Kearney, Nebraska, Feb. 26, 2005.

Bromage, Niall, et al., "The Environmental Regulation of Maturation in Farmed Finfish with Special Reference to the Role of Photoperiod and Melatonin", Aquaculture 197, Elsevier, pp. 63-98, 2001.

Davies, B., et al., "The Effects of Fluctuating Seasonal and Constant Water Temperatures on the Photoperiodic Advancement of Reproduction in Female Rainbow Trout, *Oncorhynchus mykiss*", Aquaculture 205, Elsevier, pp. 183-200, 2002.

Doyle, Roger, W., "An Approach to the Quantitative Analysis of Domestication Selection in Aquaculture", Aquaculture 33, Elsevier Science Publishers B.V., Printed in the Netherlands, pp. 167-185, 1983.

Dunham, Rex, A., et al., "Response of Two Generations of Selection to Increased Body Weight in Channel Catfish, *Ictalurus punctatus*, Compared to Hybridization with Blue Catfish, *I. furcatus*, Males," Journal of Applied Aquaculture, The Haworth Press, Inc., vol. 9(3), pp. 37-45, 1999.

Dunham, Rex, A. et al., "Response to Selection and Realized Heritability for Body Weight in Three Strains of Channel Catfish, Ictalurus Punctatus, Grown in Earthen Ponds", Aquaculture 33, Elsevier Science Publishers B.V., Amsterdam, printed in the Netherlands, pp. 89-96, 1983.

Fontaine, Pascal, et al., "Influence of Pre-Inductive Photoperiod Variations on Eurasian Perch *Perca fluviatilis* Broodstock Response to an Inductive Photothermal Program", Aquaculture 255, Elsevier, pp. 410-416, 2006.

Gjedrem, T., "Genetic Improvement of Cold-Water Fish Species", Aquaculture Research 31, pp. 25-33, 2000.

Gjerde, Bjarne, "Growth and Reproduction in Fish and Shellfish", Aquaculture 57, Elsevier Science Publishers B. V., Amsterdam, printed in The Netherlands, pp. 37-55, 1986.

Harrington, Robert W. Jr., "Observations on the Breeding Habits of the Yellow Perch, *Perca flavescens* (Mitchill)", Copeia, vol. 1947, No. 3, pp. 199-200, Sep. 12, 1947.

Heidinger, Roy, C. et al., "Yellow Perch", Culture of Non-Salmonid Freshwater Fishes, Chapter 7, pp. 103-113, 1986.

Hergenrader, Gary, L., "Spawning Behavior of *Perca flavescens* in Aquaria", Copeia, vol. 1969, No. 4, pp. 839-841, Dec. 5, 1969.

Hershberger, W.K. et al., "Genetic Changes in the Growth of Coho Salmon (*Oncorhynchus kisutch*) in Marine Net-Pens, Produced by Ten Years of Selection," Aquaculture 85, Elsevier Science Publishers B.V., Amsterdam, printed in The Netherlands, pp. 187-197, 1990.

Hokanson, Kenneth, E.F., "Temperature Requirements of Some Percids and Adaptations to the Seasonal Temperature Cycle", Journal of Fisheries Research Board of Canada, vol. 34, pp. 1524-1550, 1977.

Huff, David, D. et al., "Environmental Constraints on Spawning Depth of Yellow Perch: The Roles of Low Temperature and High Solar Ultraviolet Radiation", Transactions of the American Fisheries Society 133, pps. 718-726, 2004.

Hulata, G., "Genetic Manipulations in Aquaculture: A Review of Stock Improvement by Classical and Modern Technologies", Genetica 111, Kluwer Academic Publishers, printed in the Netherlands, pp. 155-173, 2001.

Kayes, Terrence, B., et al., "Effects of Photoperiod and Temperature on the Spawning of Yellow Perch (*Perca flavescens*)", Proc. World Mariculture Soc. 10, pp. 306-316, 1979.

Kirpichnikov, V.S., "Problems and Methods of Fish Selection", Genetic Bases of Fish Selection, Springer-Verlag, Berlin, Chapter 8, 1981.

Kolkovski, S. et al., "Off-Season Spawning of Yellow Perch", The Progressive Fish-Culturist 60, American Fisheries Society, pp. 133-136, 1998.

Le Cren, E.D., "The Length-Weight Relationship and Seasonal Cycle in Gonad Weight and Condition in the Perch (*Perca fluviatilis*)," Journal of Animal Ecology, vol. 20, No. 2, pp. 201-219, 1951.

Masuma, Shukei, et al., "Effects of Water Temperature on Bluefin Tuna Spawning Biology in Captivity", Bulletin of Fisheries Research Agency, Suppl.4, pp. 157-171, 2006.

Migaud, Herve, et al., "Induction of Out-of-Season Spawning in Eurasian Perch *Perca fluviatilis*: Effects of Rates of Cooling and Cooling Durations on Female Gametogenesis and Spawning", Aquaculture 205, Elsevier, pp. 253-267, 2002.

Migaud, Harve, et al., "Influence of Photoperiod on Reproductive Performances in Eurasian Perch *Perca fluviatilis*", Aquaculture252, Elsevier, pp. 385-393, 2006.

Migaud, Herve, et al., "Influence of Photoperiod on the Onset of Gonadogenesis in Eurasian Perch *Perca fluviatilis*", Aquaculture 241, Elsevier, pp. 561-574, 2004.

Migaud, H., et al., "Influence of Photoperiod Regimes on the Eurasian Perch Gonadogenesis and Spawning", Fish Physiology and Biochemistry 28, Kluwer Academic Publishers, printed in the Netherlands, pp. 395-397, 2003.

Migaud, Herve, et al., "Off-Season Spawning of Eurasian Perch *Perca Fluviatilis*", Aquaculture International 12, Kluwer Academic Publishers, printed in the Netherlands, pp. 87-102, 2004.

Mischke, Charles, C., et al., "Out-of-Season Spawning of Sunfish *Lepomis* spp. In the Laboratory", The Progressive Fish-Culturist 59, American Fisheries Society, pp. 297-302, 1997.

Myers, James, M. et al., "Genetics and Broodstock Management of Coho Salmon", Aquaculture 197, Elsevier, pp. 43-62, 2001.

Naze, K., "Sturgeon Science—Stocking Continues Historic Fox River Rebuilding Project," Green Bay Press Gazette, Aug. 8, 2002.

Nuese, J.C., "Development and Maintenance of Yellow Perch Broodstock", Public Presentation, Yellow Perch Workshop of the Joint Meeting of the Nebraska Aquaculture Association and the Sandhills Yellow Perch Cooperative in Kearney, Nebraska, Feb. 26, 2005.

Nuese, J.C., "Development and Maintenance of Yellow Perch Broodstock", Public Presentation, Michigan Aquaculture Association, Annual Business Conference "Sustainable Aquaculture," Lansing, Michigan, Feb. 10, 2006.

Nuese, J.C., "Development and Maintenance of Yellow Perch Brookstock", Public Presentation, Indiana Aquaculture Association Spring Meeting & Workshop, Monticello, Indiana, Mar. 18, 2006.

Nuese, J.C., "Development and Maintenance of Yellow Perch Brookstock," Public Presentation from Wisconsin Association of Agricultural Educators Advanced Aquaculture Workshop, Middleton, Wisconsin, Jun. 27, 2007.

Soderberg, Richard, W., "Perch Fingerling Production for Aquaculture," Proceedings of a Conference held at the University of Wisconsin, University of Wisconsin Sea Grant College Program Advisory Report #421, Dec. 12, 1977.

Tave, Douglas, "Genetics of Broodstock Management," Genetics for Fish Hatchery Managers, AVI Publishing Company, Inc., Westport, Connecticut, Chapter 5, 1986.

Thorpe, J, "Synopsis of Biological Data on the Perch, *Perca fluviatilis* Linnaeus, 1758 and *Perca flavescens* Mitchill, 1814," FAO Fisheries Synopsis No. 113, Food and Agriculture Organization of the United Nations, Rome, Dec. 1977.

Thorpe, J.E., "Morphology, Physiology, Behavior, and Ecology of *Perca fluviatilis* L. and *P. flavescens* Mitchill," Journal of Fisheries Research Board of Canada 34, pp. 1504-1514, 1977.

Turner, Clarence, L., "The Seasonal Cycle in the Spermary of the Perch," Journal of Morphology, The Wistar Institute of Anatomy and Biology, vol. 32, pp. 681-711, 1919.

West, Graden, et al., "Culture of Yellow Perch with Emphasis on Development of Eggs and Fry," Am. Fish. Soc. Spec. Publ. 11, pp. 175-176, 1978.

Williamson, Craig, E. et al., "Solar Ultraviolet Radiation and the Spawning Habitat of Yellow Perch, *Perca flavescens*," Ecological Applications, 7(3), pp. 1017-1023, 1997.

WATER Tours, Tours conducted at the Great Lakes WATER Institute, Wisconsin Aquatic Technology and Environmental Research, University of Wisconsin-Milwaukee/University of Wisconsin System, Milwaukee, WI, conducted since about 1988. (see Declaration Regarding Information Disclosure Statement).

* cited by examiner

METHODS FOR MANIPULATING FISH SPAWNING CYCLES

CROSS-REFERENCE TO RELATED APPLICATIONS

This application claims priority under 35 U.S.C. §119(e) to U.S. Provisional Patent Application No. 60/873,783 filed Dec. 8, 2006, the entire content of which is hereby incorporated by reference.

BACKGROUND

Economically important freshwater fish including, without limitation, yellow perch, European perch, walleye, sauger, northern pike, musky, bluegill, and crappie only spawn one time each year. Therefore, gametes can only be collected one time each year. This affects the available supply of fresh fish. Therefore, a method for developing fish that can spawn throughout the year is desirable.

SUMMARY

In one aspect, the invention provides a method of manipulating a spawning cycle of perch across multiple generations. The method includes identifying a desired out-of-cycle spawning period for perch, selecting a geographic strain of perch having a natural spawning period in proximity to the desired out-of-cycle spawning period, and developing a first generation broodstock from the geographic strain, where the broodstock's natural spawning period has been shifted to the desired spawning period using at least one of temperature and photoperiod manipulation. The method further includes identifying a second desired out-of-cycle spawning period and developing a second generation broodstock from the first generation broodstock, where the second generation broodstock's spawning period has been shifted from the desired out-of-cycle spawning period to the second desired out-of-cycle spawning period using at least one of temperature and photoperiod manipulation.

In another aspect, the invention provides a method of manipulating a spawning cycle of perch that includes selecting a strain of yellow perch from the Chesapeake Bay and manipulating at least one of temperature and photoperiod to shift the spawning cycle thereof.

In yet another aspect, the invention provides a method of manipulating a spawning cycle of perch that includes selecting a strain of yellow perch from the Sassafras River and manipulating at least one of temperature and photoperiod to shift the spawning cycle thereof.

Other aspects of the invention will become apparent by consideration of the detailed description and accompanying drawings.

DETAILED DESCRIPTION

Figure 1:
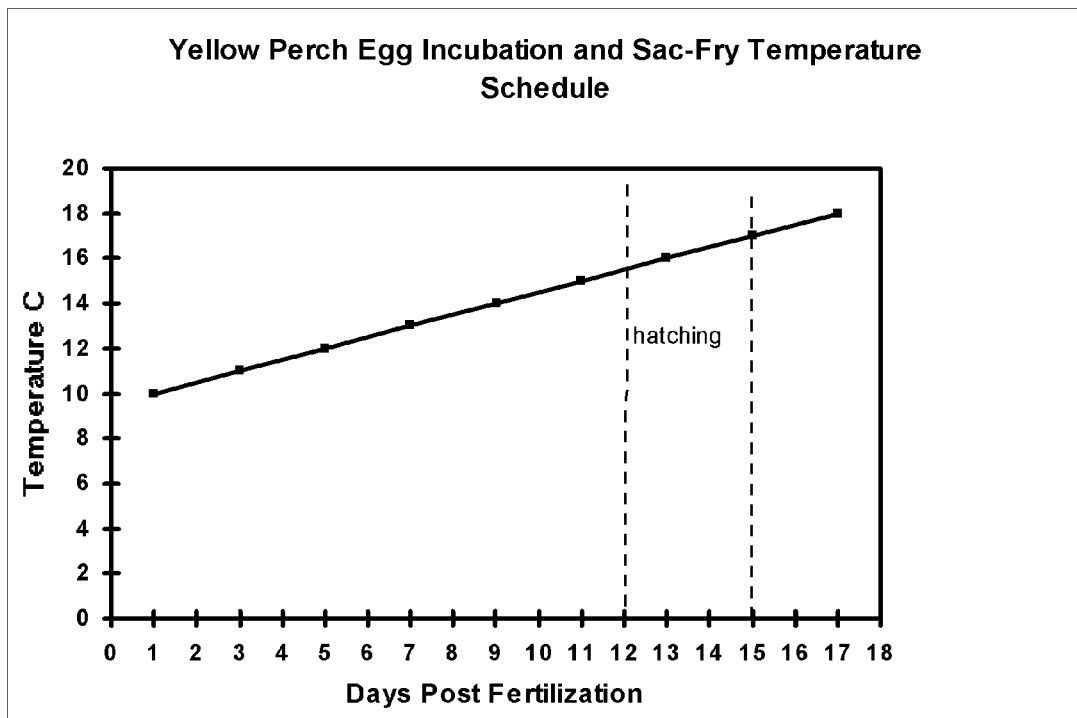
FIG. 1 is a table showing a yellow perch egg incubation temperature schedule.

Before any embodiments of the invention are explained in detail, it is to be understood that the invention is not limited in its application to the details of construction and the arrangement of components set forth in the following description. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

The present invention provides methods for changing the biological clock of fish with regard to reproduction. This process includes conditioning fish to spawn anytime on the 12 month calendar once sexual maturity is reached. Out-of-cycle spawning broodstocks can be developed to produce gametes every 2-3 months. Having gametes available this often creates an economic advantage by producing a valuable resource throughout the year.

The present invention provides for the identification and modification of water temperature or photoperiod regimes or a combination thereof to facilitate fish spawning anytime throughout the year. Although each particular broodstock will still only spawn one time each year, this process allows for the production of multiple broodstocks that each spawn at different times. A water temperature or photoperiod regime or a combination thereof is created, which "tricks" the fish into spawning at predetermined times, which are optimal for commercial production. To be successful, the development of out-of-cycle broodstock starts with the selection of the parents. Healthy and genetically diverse geographic strains must initially be used to collect gametes.

In one aspect, the invention may provide a method of advancing or retarding spawning of fish. The method may comprise manipulating temperature of water in which the fish live to advance or retard spawning. In some instances, this may be done on a commercial scale to coincide with commercial demands.

In another aspect, the invention may provide another method of advancing or retarding spawning of fish by manipulating a photoperiod to which fish are exposed to advance or retard spawning. In some instances, this may be done on a commercial scale to coincide with commercial demands.

In a further aspect, the invention may provide another method of advancing or retarding spawning of fish by manipulating temperature and photoperiod to synergistically advance or retard spawning. In some instances, this may be done on a commercial scale to coincide with commercial demands.

In yet another aspect, the invention may provide a method of advancing or retarding spawning comprising developing a yearly temperature profile using average local water temperatures for a geographic strain of fish and manipulating the temperature profile by shifting the profile forward (i.e., later) or backward (i.e., earlier) to achieve a desired spawning time.

In yet another aspect, the invention may provide a method of advancing or retarding spawning comprising developing a yearly photoperiod profile using local daily sunrise and sunset times for a geographic strain of fish and manipulating the photoperiod profile by shifting the profile forward or backward to achieve a desired spawning time. In some instances, this may be done on a commercial scale to coincide with commercial demands.

In a further aspect, the invention may provide a method of advancing or retarding spawning comprising developing a yearly temperature profile using average local water temperatures for a geographic strain of fish, developing a yearly photoperiod profile using the local daily sunrise and sunset times for a geographic strain of fish, and manipulating the temperature and photoperiod profiles by shifting the profiles forward or backward to achieve a desired spawning time.

All of these methods may further comprise selecting a geographic strain of fish for use in said methods. The methods may comprise at least one of evaluating gamete quality, evaluating fertility rate, evaluating % eye-up, evaluating hatching success, evaluating sac-fry survival, evaluating first food acceptance, evaluating swim bladder inflation, and evaluating spinal deformation, evaluating growth, evaluating post-larval survival and combination thereof.

In a further aspect, the invention may provide a method for raising domesticated broodstock. Using the $F_1$, $F_2$, $F_3$, etc. progeny from the original broodstock may result in a more advanced domesticated fish, which should better adapt to captive commercial production conditions.

In another aspect, the invention may provide a method for deciding whether to advance or retard spawning by obtaining fish eggs closest to an intended out-of-cycle spawning time and determining whether spawning should be advanced or retarded. By using the approach of using fish eggs closest to the intended out-of-cycle spawning time, the shift in months is minimized, reducing the physiological stress needed for optimal gonadal maturation.

In one embodiment, the process does not use any chemicals or hormones. There have not been any other successful attempts at inducing yellow perch (*Perca flavescens*) to spawn out-of-cycle to the extent of the present invention, which has produced tens of thousands of yellow perch fingerlings. Over 80% of the females were fully ovulated and males spermiated at close to 100%. The average fertility was greater than 90% and larval skeletal abnormalities were as low as 1%. Earlier attempts have resulted in spawning that occurs only slightly later than normal. The process can develop spawning broodstock at any time within the 12 month calendar.

As used herein, the term "broodstock" refers to a group of cohorts (geographic strain) used to produce progeny.

The development of broodstock starts with the artificial fertilization of eggs in the field from a wild population. Through years of experience, it has been determined that certain geographic strains perform better than others. In one embodiment, Great Lakes geographic strains are used, including, without limitation, strains from Green Bay. In another embodiment, United States East Coast strains are used, including, without limitation, strains from North Carolina, the Chesapeake region, the Sassafras River (Maryland), and the Choptank River (Maryland). There are strains which consistently perform poorly (low hatching success, high early mortality, poor swim bladder inflation, spinal deformities, etc.), while others always thrive in the laboratory environment. Some strains surprisingly and unexpectedly produce the best results. Examples of such strains include, without limitation, strains from the East Coast of the United States. More particularly, examples of such strains include, without limitation, strains from the Chesapeake region, the Sassafras River, and the Choptank River. It is beneficial to collect eggs and milt from geographic strains (Green Bay and Chesapeake Bay) that will yield good results. Based on laboratory research evaluations, these strains exhibit biological profiles for quality fertility, hatching success, sac fry survival, fingerling production, and growth. To increase genetic diversity, eggs are collected from as many females as possible (up to about 20 females). Eggs from each female are fertilized using 2 to 3 males, providing the potential for up to about 60 families. Using multiple males per female not only increases genetic diversity, but it also increases the chance that eggs will be fertilized if one male is sterile, has decreased sperm motility/sperm count, etc. If time and weather permit, as much information on the parents as possible is collected. The most important information collected is total length and anal spines (used for aging). The eggs are then washed and water hardened. Each fertilized egg strand is placed into a 1-2 gallon Ziploc bag with water. The Ziploc bags are placed into coolers or other insulated containers. Bags of ice are added to the coolers, but are not allowed to come into contact with the bags of eggs. This creates an environment that facilitates the eggs to remain at about 10-12° C. (optimal) during transport to the laboratory. Eggs are either next-day shipped, or driven back to the laboratory.

Upon arrival at the lab, egg volume is measured for each female and small sub-samples of eggs are enumerated. From the egg counts, the number of eggs per $cm^3$ can be estimated and used to estimate the total number of eggs brought back to the lab. The sub-samples are also used to determine fertility rates. The egg strands are stretched out and "pinned" on a suspended substrate in the incubation tank to allow oxygenated water to flow above and below. Pinning refers to attaching several areas of the egg strands to the substrate. This prevents water turbulence from moving the eggs within the tank. During incubation, the tank is covered with opaque black plastic to prevent exposure to laboratory lighting. Some studies have suggested that U.V. light has negative effects on egg development. Water temperature is increased by about 1° C. every two days until hatching begins (about 16-18° C.) (FIG. 1). Hatching occurs over a period of about 2-3 days. Near the end of hatching, a plastic rod is rapidly rotated above the remaining eggs to create turbulence. This facilitates the final eggs to hatch. When hatching is complete, temperatures are again increased by about 1° C. every two days until the summer temperature is reached (20-24° C. depending on the geographic strain of the parents).

In general, temperature cycles are identified based on the geographic strain of perch. Summer temperatures are generally about 20° C. to about 24° C. Winter temperatures are about 5° C. to about 6° C., and last for about 100 to about 180 days. Temperatures change twice a year, in spring and autumn. The temperature changes about 1° C. every 2 to 4 days for spring and autumn. Spring temperatures last for about 56 to about 60 days. Autumn temperatures last for about 42 to about 60 days. The summer season can be extended or reduced to start the autumn season at the desired out-of-cycle time. Regional temperature and photoperiod information can be found at http://waterdata.usgs.gov/nwis and http://aa.usno.navy.mil/. Photoperiod and water temperature schedules can be manipulated to push spawning forward or backward from the normal cycle. Spawning could occur in every month of the year.

Different types of rearing systems may be used. For example, without limitation, flow-through, recirculating aquaculture system (RAS), and outdoor rearing systems may be used.

Many types of foods are used in rearing fish from hatch to sexually mature adults. The goal is to get the larvae to consume 100% dry commercial food as soon as possible. Dry commercial diets are relatively inexpensive and have a minimal effect on water quality. Commercial diets are distributed using automatic feeders programmed to feed during "daylight" time. Food size is adjusted accordingly based on the gape size of the fish at any given time. If the fish are physically able to consume the next larger commercial diet size (gape limited), that diet size will start to be incorporated into the feeding regime. For example, adult fish may be fed a 6.5 mm broodstock diet (38% protein, 10% fat), sub-adult fish may be fed a 3 mm grower pellet diet (45% protein, 12% fat), fingerlings (domestic) may be fed a starter/grower diet (45-55% protein, 15% fat), and fingerlings (wild) may be fed specialty diets for training. Food is readily available from commercial vendors, or processed from raw materials in the laboratory.

Water temperature is recorded daily and is adjusted as needed to remain within the scheduled seasonal temperature regime. Photoperiods are adjusted once per week in accordance with their regime. Tank lighting is adjusted (turned on and off) using electric timers. Once local sunrise and sunset times are established for the geographic area of the strain, they are entered into the timers. The photoperiod timers are adjusted (corrected) once per week to maintain accurate photoperiods.

To successfully develop an out-of-cycle spawning broodstock, fertilized eggs from a geographic strain of yellow perch that naturally spawns closest to the intended out-of-cycle spawning time may be obtained. For example, to develop an August spawning broodstock, it is better to use fertilized eggs from a wild Lake Michigan, Wis. (June spawning) strain than to use a wild Sassafras River or North Carolina (March spawning) strain. In some aspects, a geographic strain of perch is selected that has a natural spawning period within a 4 or 3 month proximity to the desired out-of-cycle spawning period. In other aspects, a geographic strain of perch is selected that has a natural spawning period within a 2 or 1 month proximity to the desired out-of-cycle spawning period. However, a larger range can be successful if it is done over multiple generations. In the above example, the Sassafras River or North Carolina strain could be used to develop a June spawning broodstock. That June spawning broodstock would produce offspring that could be developed into an August spawning broodstock. Although this would take two generations to complete, the Sassafras River or North Carolina strain may have more desirable traits than the Lake Michigan strain to some producers. Manipulating the spawning cycles of perch across multiple generations may be performed on a commercial scale.

There are many ways to quantify the success of normal and out-of-cycle spawning broodstocks. The first is to measure the Gonadal Somatic Index (GSI), which is the mass of gonadal tissue per body weight. This will determine how well the broodstock is developing actual gonadal tissue. The gamete quality can be measured using biochemical and molecular techniques to determine the proximate composition of fertilized eggs. Fertility rate can be determined by looking at the eggs under a dissecting microscope and recording the fertilized vs. non-fertilized eggs. Fertility rate could be affected by the quality of eggs or milt, physical abuse, or water quality. Hatching success can be measured as well. Although fertilization, embryo development, and hatching success are very significant factors in evaluating broodstock success, post-hatch survival and growth are equally as important. The most critical post-hatch developmental process is swim bladder inflation. It occurs early in larval development (7-12 days post hatch), and is very important to the overall success of a group of cohorts. Poor/no swim bladder inflation will not directly kill fish. However, it generally will cause slow growth, spinal deformations, poor food conversion, or could result in being isolated and cannibalized. None of these qualities are beneficial to a yellow perch producer. Swim bladder inflation problems have been linked to geographic strains, and should be considered when selecting gametes to develop domesticated yellow perch broodstocks. When the offspring are large enough to collect DNA samples from, the genetic variability can be measured for parental input. The offspring could be from only a couple females (low diversity), or many females (high diversity). Lower diversity could indicate a low fertility rate in that particular strain. Yellow perch broodstocks tend to improve their biological characteristics as they become more domesticated. Examples of biological characteristics include, without limitation, fertility, hatching success, sac fry survival, fingerling production, and growth. The fish that thrive in a captive environment tend to become a better broodstock. Over time, those that thrive will pass on "captive genes" to their offspring, resulting in a generation that is even more domesticated and better adapted at being a captive broodstock. This becomes a form of passive genetic selection/selective breeding that will benefit each producer individually based on the unique characteristics of their facility.

The development of out-of-cycle spawning yellow perch is dependent on the control of water temperature, photoperiod, or a combination thereof.

EXAMPLES

Example 1

Figure 2:
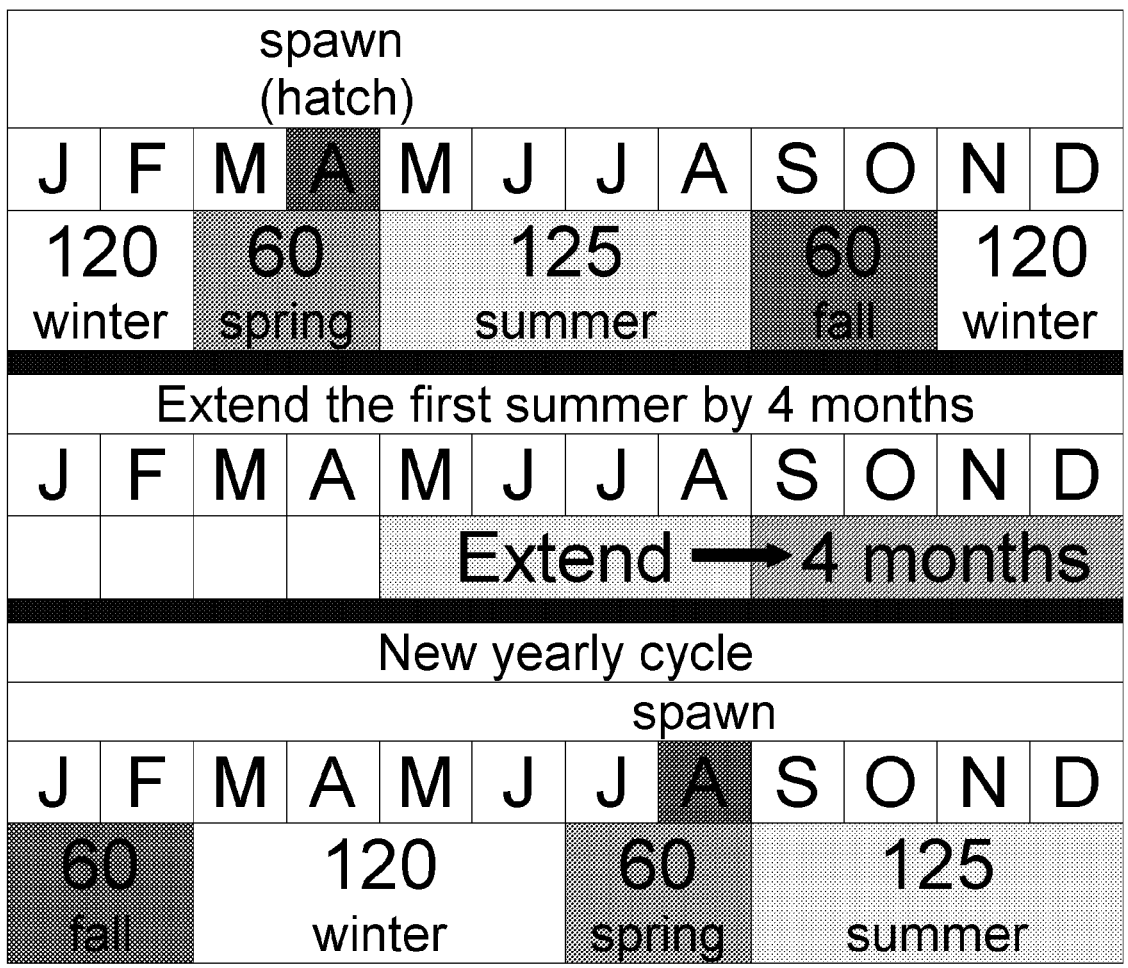
FIG. 2 is a table showing shifting a spawning cycle forward for offspring of the Green Bay strain of yellow perch.

Yellow perch spawn when the water temperature rises to about 10-12° C. in the spring. In the following example, the Green Bay, Wis. strain (normal April spawners) was used to develop an August spawning out-of-cycle broodstock (FIG. 2). In FIG. 2, the season lengths (water temperatures) are simplified for easier visualization of shifting. The Green Bay strain was selected for its biological characteristics and because its natural spawning time is in proximity to the desired out-of-cycle spawning time of August. Eggs were fertilized in the field (Green Bay) and brought back to the lab. The egg incubation and post-hatch water temperature schedule previously discussed was followed (FIG. 1). A yearly temperature and photoperiod profile was developed based on the geographic strain's local average conditions (Green Bay, Wis.). The photoperiod profile is simply the daily sunrise and sunset times for the strain's local area over a year. The water temperature profile must be developed using average local water temperatures throughout the year. Refer to FIG. 2 for the following narrative. Once the eggs hatched and normal summer temperatures were reached, those summer temperatures and photoperiods would normally be maintained until September before the autumn begins. However, the development of an August spawning broodstock (4 months later than normal) was desired. So, rather than the autumn beginning in September, the first summer after hatch was extended another 4 months. The summer water temperatures and photoperiods were maintained for an extra 4 months. In addition, the entire yearly local temperature and photoperiod profiles were shifted forward by 4 months. The new autumn then began in January rather than September, and the new spring began in July rather than March. This "tricked" the fish into thinking they were spawning in the spring, when in reality it was 4 months past normal spawning. The local temperature and photoperiod profiles were shifted by 4 months in every subsequent year. This is an example of shifting a cycle forward.

Example 2

Figure 3:
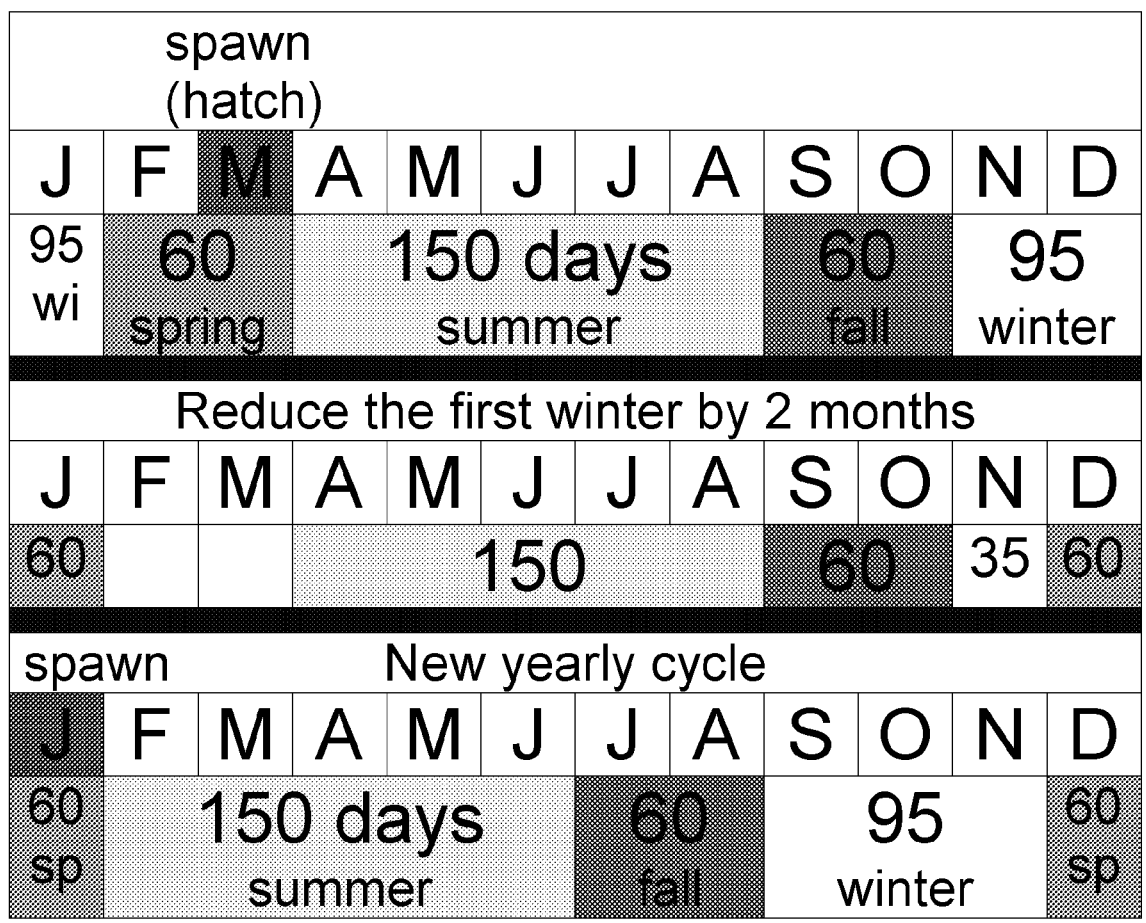
FIG. 3 is a table showing shifting a spawning cycle backward for offspring of the Chesapeake strain of yellow perch.

A broodstock can also be shifted backward to produce an earlier spawning broodstock. In this example, the Chesapeake strain, particularly, the Sassafras River strain, (normal March spawning) of yellow perch was used to develop a January out-of-cycle broodstock (FIG. 3). In FIG. 3, the season lengths (water temperatures) are simplified for easier visualization of shifting. The Chesapeake strain, which spawns in March, was selected for its biological characteristics and because its natural spawning time is in proximity to the desired out-of-cycle spawning time of January. Again, yearly local photoperiod and water temperature profiles were identified. In this example, rather than increasing the first summer, the first winter was decreased by 2 months to allow the new spring to begin in December rather than in February. The local temperature and photoperiod profiles were used from that point on, but they were shifted back 2 months. Further details are set forth in Table 1. The project was undertaken and continues as set forth in Table 1. Depending on the strain, the offspring become sexually mature by about 2 to 3 years of age. By comparing FIG. 2 and FIG. 3, it is obvious that the season lengths (water temperatures) are different between them. This is due to the local profiles. Green Bay, Wis. is going to have a longer winter and shorter summer than the Chesapeake area of Delaware/Maryland.

TABLE 1

Chesapeake Strain Yellow Perch Broodstock January Spawners
(Adjusted to Local Avg. Temps)
(From Chesapeake Normal March Spawners)

| Date | Temp Range | Temp Flow | Comments |
|---|---|---|---|
| Mar. 10, 2007 | 10-12 | | ESTIMATED NORMAL SPAWN & EGG COLLECTION |
| Mar. 11, 2007 | 10-12 | | |
| Mar. 12, 2007 | 11-13 | | |
| Mar. 13, 2007 | 11-13 | | |
| Mar. 14, 2007 | 12-14 | | |
| Mar. 15, 2007 | 12-14 | | |
| Mar. 16, 2007 | 13-15 | | |
| Mar. 17, 2007 | 13-15 | | |
| Mar. 18, 2007 | 14-16 | | |
| Mar. 19, 2007 | 14-16 | | |
| Mar. 20, 2007 | 15-17 | | |
| Mar. 21, 2007 | 15-17 | | |
| Mar. 22, 2007 | 16-18 | | |
| Mar. 23, 2007 | 16-18 | | ESTIMATED HATCH |
| Mar. 24, 2007 | 17-19 | | |
| Mar. 25, 2007 | 17-19 | | |
| Mar. 26, 2007 | 18-20 | | |
| Mar. 27, 2007 | 18-20 | | |
| Mar. 28, 2007 | 19-21 | | |
| Mar. 29, 2007 | 19-21 | | |
| Mar. 30, 2007 | 20-22 | | |
| Mar. 31, 2007 | 20-22 | | |
| Apr. 1, 2007 | 20-22 | | |
| Apr. 2, 2007 | 20-22 | | |
| Apr. 3, 2007 | 20-22 | | |
| Apr. 4, 2007 | 20-22 | | |
| Apr. 5, 2007 | 20-22 | | |
| Apr. 6, 2007 | 20-22 | | |
| Apr. 7, 2007 | 20-22 | | |
| Apr. 8, 2007 | 20-22 | | |
| Apr. 9, 2007 | 20-22 | | |
| Apr. 10, 2007 | 20-22 | | |
| Apr. 11, 2007 | 20-22 | | |
| Apr. 12, 2007 | 20-22 | | |

TABLE 1-continued

Chesapeake Strain Yellow Perch Broodstock January Spawners
(Adjusted to Local Avg. Temps)
(From Chesapeake Normal March Spawners)

| Date | Temp Range | Temp Flow | Comments |
|---|---|---|---|
| Apr. 13, 2007 | 20-22 | | |
| Apr. 14, 2007 | 20-22 | | |
| Apr. 15, 2007 | 20-22 | | |
| Apr. 16, 2007 | 20-22 | | |
| Apr. 17, 2007 | 20-22 | | |
| Apr. 18, 2007 | 20-22 | | |
| Apr. 19, 2007 | 20-22 | | |
| Apr. 20, 2007 | 20-22 | | |
| Apr. 21, 2007 | 20-22 | | |
| Apr. 22, 2007 | 20-22 | | |
| Apr. 23, 2007 | 20-22 | | |
| Apr. 24, 2007 | 20-22 | | |
| Apr. 25, 2007 | 20-22 | | |
| Apr. 26, 2007 | 20-22 | | |
| Apr. 27, 2007 | 20-22 | | |
| Apr. 28, 2007 | 20-22 | | |
| Apr. 29, 2007 | 20-22 | | |
| Apr. 30, 2007 | 21-23 | | |
| May 1, 2007 | 21-23 | | |
| May 2, 2007 | 21-23 | | |
| May 3, 2007 | 21-23 | | |
| May 4, 2007 | 21-23 | | |
| May 5, 2007 | 21-23 | | |
| May 6, 2007 | 21-23 | | |
| May 7, 2007 | 21-23 | | |
| May 8, 2007 | 21-23 | | |
| May 9, 2007 | 21-23 | | |
| May 10, 2007 | 21-23 | | |
| May 11, 2007 | 21-23 | | |
| May 12, 2007 | 21-23 | | |
| May 13, 2007 | 21-23 | | |
| May 14, 2007 | 21-23 | | |
| May 15, 2007 | 21-23 | | |
| May 16, 2007 | 21-23 | | |
| May 17, 2007 | 21-23 | | |
| May 18, 2007 | 21-23 | | |
| May 19, 2007 | 21-23 | | |
| May 20, 2007 | 21-23 | | |
| May 21, 2007 | 21-23 | | |
| May 22, 2007 | 21-23 | | |
| May 23, 2007 | 21-23 | | |
| May 24, 2007 | 21-23 | | |
| May 25, 2007 | 22-24 | | |
| May 26, 2007 | 22-24 | | |
| May 27, 2007 | 22-24 | | |
| May 28, 2007 | 22-24 | | |
| May 29, 2007 | 22-24 | | |
| May 30, 2007 | 22-24 | | |
| May 31, 2007 | 22-24 | | |
| Jun. 1, 2007 | 22-24 | | |
| Jun. 2, 2007 | 22-24 | | |
| Jun. 3, 2007 | 22-24 | | |
| Jun. 4, 2007 | 22-24 | | |
| Jun. 5, 2007 | 22-24 | | |
| Jun. 6, 2007 | 22-24 | | |
| Jun. 7, 2007 | 22-24 | | |
| Jun. 8, 2007 | 22-24 | | |
| Jun. 9, 2007 | 22-24 | | |
| Jun. 10, 2007 | 22-24 | | |
| Jun. 11, 2007 | 22-24 | | |
| Jun. 12, 2007 | 22-24 | | |
| Jun. 13, 2007 | 22-24 | | |
| Jun. 14, 2007 | 22-24 | | |
| Jun. 15, 2007 | 22-24 | | |
| Jun. 16, 2007 | 22-24 | | |
| Jun. 17, 2007 | 22-24 | | |
| Jun. 18, 2007 | 22-24 | | |
| Jun. 19, 2007 | 22-24 | | |
| Jun. 20, 2007 | 22-24 | | |
| Jun. 21, 2007 | 22-24 | | |
| Jun. 22, 2007 | 22-24 | | |
| Jun. 23, 2007 | 22-24 | | |

TABLE 1-continued

Chesapeake Strain Yellow Perch Broodstock January Spawners
(Adjusted to Local Avg. Temps)
(From Chesapeake Normal March Spawners)

| Date | Temp Range | Temp Flow | Comments |
|---|---|---|---|
| Jun. 24, 2007 | 22-24 | | |
| Jun. 25, 2007 | 22-24 | | |
| Jun. 26, 2007 | 22-24 | | |
| Jun. 27, 2007 | 22-24 | | |
| Jun. 28, 2007 | 22-24 | | |
| Jun. 29, 2007 | 22-24 | | |
| Jun. 30, 2007 | 22-24 | | |
| Jul. 1, 2007 | 22-24 | | |
| Jul. 2, 2007 | 22-24 | | |
| Jul. 3, 2007 | 22-24 | | |
| Jul. 4, 2007 | 22-24 | | |
| Jul. 5, 2007 | 22-24 | | |
| Jul. 6, 2007 | 22-24 | | |
| Jul. 7, 2007 | 22-24 | | |
| Jul. 8, 2007 | 22-24 | | |
| Jul. 9, 2007 | 22-24 | | |
| Jul. 10, 2007 | 22-24 | | |
| Jul. 11, 2007 | 22-24 | | |
| Jul. 12, 2007 | 22-24 | | |
| Jul. 13, 2007 | 22-24 | | |
| Jul. 14, 2007 | 22-24 | | |
| Jul. 15, 2007 | 21-23 | | |
| Jul. 16, 2007 | 21-23 | | |
| Jul. 17, 2007 | 21-23 | | |
| Jul. 18, 2007 | 21-23 | | |
| Jul. 19, 2007 | 21-23 | | |
| Jul. 20, 2007 | 21-23 | | |
| Jul. 21, 2007 | 21-23 | | |
| Jul. 22, 2007 | 21-23 | | |
| Jul. 23, 2007 | 21-23 | | |
| Jul. 24, 2007 | 21-23 | | |
| Jul. 25, 2007 | 21-23 | | |
| Jul. 26, 2007 | 21-23 | | |
| Jul. 27, 2007 | 21-23 | | |
| Jul. 28, 2007 | 21-23 | | |
| Jul. 29, 2007 | 21-23 | | |
| Jul. 30, 2007 | 21-23 | | |
| Jul. 31, 2007 | 21-23 | | |
| Aug. 1, 2007 | 21-23 | | |
| Aug. 2, 2007 | 21-23 | | |
| Aug. 3, 2007 | 21-23 | | |
| Aug. 4, 2007 | 21-23 | | |
| Aug. 5, 2007 | 21-23 | | |
| Aug. 6, 2007 | 21-23 | | |
| Aug. 7, 2007 | 21-23 | | |
| Aug. 8, 2007 | 21-23 | | |
| Aug. 9, 2007 | 21-23 | | |
| Aug. 10, 2007 | 20-22 | | |
| Aug. 11, 2007 | 20-22 | | |
| Aug. 12, 2007 | 20-22 | | |
| Aug. 13, 2007 | 20-22 | | |
| Aug. 14, 2007 | 20-22 | | |
| Aug. 15, 2007 | 20-22 | | |
| Aug. 16, 2007 | 20-22 | | |
| Aug. 17, 2007 | 20-22 | | |
| Aug. 18, 2007 | 20-22 | | |
| Aug. 19, 2007 | 20-22 | | |
| Aug. 20, 2007 | 20-22 | | |
| Aug. 21, 2007 | 20-22 | | |
| Aug. 22, 2007 | 20-22 | | |
| Aug. 23, 2007 | 20-22 | | |
| Aug. 24, 2007 | 20-22 | | |
| Aug. 25, 2007 | 20-22 | | |
| Aug. 26, 2007 | 20-22 | | |
| Aug. 27, 2007 | 20-22 | | |
| Aug. 28, 2007 | 20-22 | | |
| Aug. 29, 2007 | 20-22 | | |
| Aug. 30, 2007 | 20-22 | | |
| Aug. 31, 2007 | 20-22 | | |
| Sep. 1, 2007 | 20-22 | | |
| Sep. 2, 2007 | 20-22 | | |
| Sep. 3, 2007 | 20-22 | | |
| Sep. 4, 2007 | 19-21 | | |
| Sep. 5, 2007 | 19-21 | | |
| Sep. 6, 2007 | 19-21 | | |
| Sep. 7, 2007 | 19-21 | | |
| Sep. 8, 2007 | 18-20 | | |
| Sep. 9, 2007 | 18-20 | | |
| Sep. 10, 2007 | 18-20 | | |
| Sep. 11, 2007 | 18-20 | | |
| Sep. 12, 2007 | 17-19 | | |
| Sep. 13, 2007 | 17-19 | | |
| Sep. 14, 2007 | 17-19 | | |
| Sep. 15, 2007 | 17-19 | | |
| Sep. 16, 2007 | 16-18 | | |
| Sep. 17, 2007 | 16-18 | | |
| Sep. 18, 2007 | 16-18 | | |
| Sep. 19, 2007 | 16-18 | | |
| Sep. 20, 2007 | 15-17 | | |
| Sep. 21, 2007 | 15-17 | | |
| Sep. 22, 2007 | 15-17 | | |
| Sep. 23, 2007 | 15-17 | | |
| Sep. 24, 2007 | 14-16 | | |
| Sep. 25, 2007 | 14-16 | | |
| Sep. 26, 2007 | 14-16 | | |
| Sep. 27, 2007 | 14-16 | | |
| Sep. 28, 2007 | 13-15 | | |
| Sep. 29, 2007 | 13-15 | | |
| Sep. 30, 2007 | 13-15 | | |
| Oct. 1, 2007 | 13-15 | | |
| Oct. 2, 2007 | 12-14 | | |
| Oct. 3, 2007 | 12-14 | | |
| Oct. 4, 2007 | 12-14 | | |
| Oct. 5, 2007 | 12-14 | | |
| Oct. 6, 2007 | 11-13 | | |
| Oct. 7, 2007 | 11-13 | | |
| Oct. 8, 2007 | 11-13 | | |
| Oct. 9, 2007 | 11-13 | | |
| Oct. 10, 2007 | 10-12 | | |
| Oct. 11, 2007 | 10-12 | | |
| Oct. 12, 2007 | 10-12 | | |
| Oct. 13, 2007 | 10-12 | | |
| Oct. 14, 2007 | 9-11 | | |
| Oct. 15, 2007 | 9-11 | | |
| Oct. 16, 2007 | 9-11 | | |
| Oct. 17, 2007 | 9-11 | | |
| Oct. 18, 2007 | 8-10 | | |
| Oct. 19, 2007 | 8-10 | | |
| Oct. 20, 2007 | 8-10 | | |
| Oct. 21, 2007 | 8-10 | | |
| Oct. 22, 2007 | 7-9 | | |
| Oct. 23, 2007 | 7-9 | | |
| Oct. 24, 2007 | 7-9 | | |
| Oct. 25, 2007 | 7-9 | | |
| Oct. 26, 2007 | 6-8 | | |
| Oct. 27, 2007 | 6-8 | | |
| Oct. 28, 2007 | 6-8 | | |
| Oct. 29, 2007 | 6-8 | | |
| Oct. 30, 2007 | 5-7 | | |
| Oct. 31, 2007 | 5-7 | | |
| Nov. 1, 2007 | 5-7 | | |
| Nov. 2, 2007 | 5-7 | | |
| Nov. 3, 2007 | 5-6 | | |
| Nov. 4, 2007 | 5-6 | | |
| Nov. 5, 2007 | 5-6 | | |
| Nov. 6, 2007 | 5-6 | | |
| Nov. 7, 2007 | 5-6 | | |
| Nov. 8, 2007 | 5-6 | | |
| Nov. 9, 2007 | 5-6 | | |
| Nov. 10, 2007 | 5-6 | | |
| Nov. 11, 2007 | 5-6 | | |
| Nov. 12, 2007 | 5-6 | | |
| Nov. 13, 2007 | 5-6 | | |
| Nov. 14, 2007 | 5-6 | | |

TABLE 1-continued

Chesapeake Strain Yellow Perch Broodstock January Spawners
(Adjusted to Local Avg. Temps)
(From Chesapeake Normal March Spawners)

| Date | Temp Range | Temp Flow | Comments |
|---|---|---|---|
| Nov. 15, 2007 | 5-6 | | |
| Nov. 16, 2007 | 5-6 | | |
| Nov. 17, 2007 | 5-6 | | |
| Nov. 18, 2007 | 5-6 | | |
| Nov. 19, 2007 | 5-6 | | |
| Nov. 20, 2007 | 5-6 | | |
| Nov. 21, 2007 | 5-6 | | |
| Nov. 22, 2007 | 5-6 | | |
| Nov. 23, 2007 | 5-6 | | |
| Nov. 24, 2007 | 5-6 | | |
| Nov. 25, 2007 | 5-6 | | |
| Nov. 26, 2007 | 5-6 | | |
| Nov. 27, 2007 | 5-6 | | |
| Nov. 28, 2007 | 5-6 | | |
| Nov. 29, 2007 | 5-6 | | |
| Nov. 30, 2007 | 5-6 | | |
| Dec. 1, 2007 | 5-6 | | |
| Dec. 2, 2007 | 5-6 | | |
| Dec. 3, 2007 | 5-6 | | Shortened 1st winter to shift into new January out-of-cycle |
| Dec. 4, 2007 | 5-7 | | |
| Dec. 5, 2007 | 5-7 | | |
| Dec. 6, 2007 | 5-7 | | |
| Dec. 7, 2007 | 5-7 | | |
| Dec. 8, 2007 | 6-8 | | |
| Dec. 9, 2007 | 6-8 | | |
| Dec. 10, 2007 | 6-8 | | |
| Dec. 11, 2007 | 6-8 | | |
| Dec. 12, 2007 | 7-9 | | |
| Dec. 13, 2007 | 7-9 | | |
| Dec. 14, 2007 | 7-9 | | |
| Dec. 15, 2007 | 7-9 | | |
| Dec. 16, 2007 | 8-10 | | |
| Dec. 17, 2007 | 8-10 | | |
| Dec. 18, 2007 | 8-10 | | |
| Dec. 19, 2007 | 8-10 | | |
| Dec. 20, 2007 | 9-11 | | |
| Dec. 21, 2007 | 9-11 | | |
| Dec. 22, 2007 | 9-11 | | |
| Dec. 23, 2007 | 9-11 | | |
| Dec. 24, 2007 | 10-12 | | |
| Dec. 25, 2007 | 10-12 | | |
| Dec. 26, 2007 | 10-12 | | |
| Dec. 27, 2007 | 10-12 | | |
| Dec. 28, 2007 | 11-13 | | |
| Dec. 29, 2007 | 11-13 | | |
| Dec. 30, 2007 | 11-13 | | |
| Dec. 31, 2007 | 11-13 | | |
| Jan. 1, 2008 | 12-14 | | |
| Jan. 2, 2008 | 12-14 | | |
| Jan. 3, 2008 | 12-14 | | |
| Jan. 4, 2008 | 12-14 | | |
| Jan. 5, 2008 | 13-15 | | |
| Jan. 6, 2008 | 13-15 | | |
| Jan. 7, 2008 | 13-15 | | |
| Jan. 8, 2008 | 13-15 | | |
| Jan. 9, 2008 | 14-16 | | |
| Jan. 10, 2008 | 14-16 | | |
| Jan. 11, 2008 | 14-16 | | |
| Jan. 12, 2008 | 14-16 | | |
| Jan. 13, 2008 | 15-17 | | |
| Jan. 14, 2008 | 15-17 | | |
| Jan. 15, 2008 | 15-17 | | |
| Jan. 16, 2008 | 15-17 | | |
| Jan. 17, 2008 | 16-18 | | |
| Jan. 18, 2008 | 16-18 | | |
| Jan. 19, 2008 | 16-18 | | |
| Jan. 20, 2008 | 16-18 | | |
| Jan. 21, 2008 | 17-19 | | |
| Jan. 22, 2008 | 17-19 | | |
| Jan. 23, 2008 | 17-19 | | |
| Jan. 24, 2008 | 17-19 | | |
| Jan. 25, 2008 | 18-20 | | |
| Jan. 26, 2008 | 18-20 | | |
| Jan. 27, 2008 | 18-20 | | |
| Jan. 28, 2008 | 18-20 | | |
| Jan. 29, 2008 | 19-21 | | |
| Jan. 30, 2008 | 19-21 | | |
| Jan. 31, 2008 | 19-21 | | |
| Feb. 1, 2008 | 19-21 | | |
| Feb. 2, 2008 | 20-22 | | |
| Feb. 3, 2008 | 20-22 | | |
| Feb. 4, 2008 | 20-22 | | |
| Feb. 5, 2008 | 20-22 | | |
| Feb. 6, 2008 | 20-22 | | |
| Feb. 7, 2008 | 20-22 | | |
| Feb. 8, 2008 | 20-22 | | |
| Feb. 9, 2008 | 20-22 | | |
| Feb. 10, 2008 | 20-22 | | |
| Feb. 11, 2008 | 20-22 | | |
| Feb. 12, 2008 | 20-22 | | |
| Feb. 13, 2008 | 20-22 | | |
| Feb. 14, 2008 | 20-22 | | |
| Feb. 15, 2008 | 20-22 | | |
| Feb. 16, 2008 | 20-22 | | |
| Feb. 17, 2008 | 20-22 | | |
| Feb. 18, 2008 | 20-22 | | |
| Feb. 19, 2008 | 20-22 | | |
| Feb. 20, 2008 | 20-22 | | |
| Feb. 21, 2008 | 20-22 | | |
| Feb. 22, 2008 | 20-22 | | |
| Feb. 23, 2008 | 20-22 | | |
| Feb. 24, 2008 | 20-22 | | |
| Feb. 25, 2008 | 20-22 | | |
| Feb. 26, 2008 | 20-22 | | |
| Feb. 27, 2008 | 21-23 | | |
| Feb. 28, 2008 | 21-23 | | |
| Feb. 29, 2008 | 21-23 | | |
| Mar. 1, 2008 | 21-23 | | |
| Mar. 2, 2008 | 21-23 | | |
| Mar. 3, 2008 | 21-23 | | |
| Mar. 4, 2008 | 21-23 | | |
| Mar. 5, 2008 | 21-23 | | |
| Mar. 6, 2008 | 21-23 | | |
| Mar. 7, 2008 | 21-23 | | |
| Mar. 8, 2008 | 21-23 | | |
| Mar. 9, 2008 | 21-23 | | |
| Mar. 10, 2008 | 21-23 | | |
| Mar. 11, 2008 | 21-23 | | |
| Mar. 12, 2008 | 21-23 | | |
| Mar. 13, 2008 | 21-23 | | |
| Mar. 14, 2008 | 21-23 | | |
| Mar. 15, 2008 | 21-23 | | |
| Mar. 16, 2008 | 21-23 | | |
| Mar. 17, 2008 | 21-23 | | |
| Mar. 18, 2008 | 21-23 | | |
| Mar. 19, 2008 | 21-23 | | |
| Mar. 20, 2008 | 21-23 | | |
| Mar. 21, 2008 | 21-23 | | |
| Mar. 22, 2008 | 21-23 | | |
| Mar. 23, 2008 | 22-24 | | |
| Mar. 24, 2008 | 22-24 | | |
| Mar. 25, 2008 | 22-24 | | |
| Mar. 26, 2008 | 22-24 | | |
| Mar. 27, 2008 | 22-24 | | |
| Mar. 28, 2008 | 22-24 | | |
| Mar. 29, 2008 | 22-24 | | |
| Mar. 30, 2008 | 22-24 | | |
| Mar. 31, 2008 | 22-24 | | |
| Apr. 1, 2008 | 22-24 | | |
| Apr. 2, 2008 | 22-24 | | |
| Apr. 3, 2008 | 22-24 | | |
| Apr. 4, 2008 | 22-24 | | |
| Apr. 5, 2008 | 22-24 | | |

TABLE 1-continued

Chesapeake Strain Yellow Perch Broodstock January Spawners
(Adjusted to Local Avg. Temps)
(From Chesapeake Normal March Spawners)

| Date | Temp Range | Temp Flow | Comments |
|---|---|---|---|
| Apr. 6, 2008 | 22-24 | | |
| Apr. 7, 2008 | 22-24 | | |
| Apr. 8, 2008 | 22-24 | | |
| Apr. 9, 2008 | 22-24 | | |
| Apr. 10, 2008 | 22-24 | | |
| Apr. 11, 2008 | 22-24 | | |
| Apr. 12, 2008 | 22-24 | | |
| Apr. 13, 2008 | 22-24 | | |
| Apr. 14, 2008 | 22-24 | | |
| Apr. 15, 2008 | 22-24 | | |
| Apr. 16, 2008 | 22-24 | | |
| Apr. 17, 2008 | 22-24 | | |
| Apr. 18, 2008 | 22-24 | | |
| Apr. 19, 2008 | 22-24 | | |
| Apr. 20, 2008 | 22-24 | | |
| Apr. 21, 2008 | 22-24 | | |
| Apr. 22, 2008 | 22-24 | | |
| Apr. 23, 2008 | 22-24 | | |
| Apr. 24, 2008 | 22-24 | | |
| Apr. 25, 2008 | 22-24 | | |
| Apr. 26, 2008 | 22-24 | | |
| Apr. 27, 2008 | 22-24 | | |
| Apr. 28, 2008 | 22-24 | | |
| Apr. 29, 2008 | 22-24 | | |
| Apr. 30, 2008 | 22-24 | | |
| May 1, 2008 | 22-24 | | |
| May 2, 2008 | 22-24 | | |
| May 3, 2008 | 22-24 | | |
| May 4, 2008 | 22-24 | | |
| May 5, 2008 | 22-24 | | |
| May 6, 2008 | 22-24 | | |
| May 7, 2008 | 22-24 | | |
| May 8, 2008 | 22-24 | | |
| May 9, 2008 | 22-24 | | |
| May 10, 2008 | 22-24 | | |
| May 11, 2008 | 22-24 | | |
| May 12, 2008 | 22-24 | | |
| May 13, 2008 | 21-23 | | |
| May 14, 2008 | 21-23 | | |
| May 15, 2008 | 21-23 | | |
| May 16, 2008 | 21-23 | | |
| May 17, 2008 | 21-23 | | |
| May 18, 2008 | 21-23 | | |
| May 19, 2008 | 21-23 | | |
| May 20, 2008 | 21-23 | | |
| May 21, 2008 | 21-23 | | |
| May 22, 2008 | 21-23 | | |
| May 23, 2008 | 21-23 | | |
| May 24, 2008 | 21-23 | | |
| May 25, 2008 | 21-23 | | |
| May 26, 2008 | 21-23 | | |
| May 27, 2008 | 21-23 | | |
| May 28, 2008 | 21-23 | | |
| May 29, 2008 | 21-23 | | |
| May 30, 2008 | 21-23 | | |
| May 31, 2008 | 21-23 | | |
| Jun. 1, 2008 | 21-23 | | |
| Jun. 2, 2008 | 21-23 | | |
| Jun. 3, 2008 | 21-23 | | |
| Jun. 4, 2008 | 21-23 | | |
| Jun. 5, 2008 | 21-23 | | |
| Jun. 6, 2008 | 21-23 | | |
| Jun. 7, 2008 | 21-23 | | |
| Jun. 8, 2008 | 20-22 | | |
| Jun. 9, 2008 | 20-22 | | |
| Jun. 10, 2008 | 20-22 | | |
| Jun. 11, 2008 | 20-22 | | |
| Jun. 12, 2008 | 20-22 | | |
| Jun. 13, 2008 | 20-22 | | |
| Jun. 14, 2008 | 20-22 | | |
| Jun. 15, 2008 | 20-22 | | |
| Jun. 16, 2008 | 20-22 | | |
| Jun. 17, 2008 | 20-22 | | |
| Jun. 18, 2008 | 20-22 | | |
| Jun. 19, 2008 | 20-22 | | |
| Jun. 20, 2008 | 20-22 | | |
| Jun. 21, 2008 | 20-22 | | |
| Jun. 22, 2008 | 20-22 | | |
| Jun. 23, 2008 | 20-22 | | |
| Jun. 24, 2008 | 20-22 | | |
| Jun. 25, 2008 | 20-22 | | |
| Jun. 26, 2008 | 20-22 | | |
| Jun. 27, 2008 | 20-22 | | |
| Jun. 28, 2008 | 20-22 | | |
| Jun. 29, 2008 | 20-22 | | |
| Jun. 30, 2008 | 20-22 | | |
| Jul. 1, 2008 | 20-22 | | |
| Jul. 2, 2008 | 20-22 | | |
| Jul. 3, 2008 | 19-21 | | |
| Jul. 4, 2008 | 19-21 | | |
| Jul. 5, 2008 | 19-21 | | |
| Jul. 6, 2008 | 19-21 | | |
| Jul. 7, 2008 | 18-20 | | |
| Jul. 8, 2008 | 18-20 | | |
| Jul. 9, 2008 | 18-20 | | |
| Jul. 10, 2008 | 18-20 | | |
| Jul. 11, 2008 | 17-19 | | |
| Jul. 12, 2008 | 17-19 | | |
| Jul. 13, 2008 | 17-19 | | |
| Jul. 14, 2008 | 17-19 | | |
| Jul. 15, 2008 | 16-18 | | |
| Jul. 16, 2008 | 16-18 | | |
| Jul. 17, 2008 | 16-18 | | |
| Jul. 18, 2008 | 16-18 | | |
| Jul. 19, 2008 | 15-17 | | |
| Jul. 20, 2008 | 15-17 | | |
| Jul. 21, 2008 | 15-17 | | |
| Jul. 22, 2008 | 15-17 | | |
| Jul. 23, 2008 | 14-16 | | |
| Jul. 24, 2008 | 14-16 | | |
| Jul. 25, 2008 | 14-16 | | |
| Jul. 26, 2008 | 14-16 | | |
| Jul. 27, 2008 | 13-15 | | |
| Jul. 28, 2008 | 13-15 | | |
| Jul. 29, 2008 | 13-15 | | |
| Jul. 30, 2008 | 13-15 | | |
| Jul. 31, 2008 | 12-14 | | |
| Aug. 1, 2008 | 12-14 | | |
| Aug. 2, 2008 | 12-14 | | |
| Aug. 3, 2008 | 12-14 | | |
| Aug. 4, 2008 | 11-13 | | |
| Aug. 5, 2008 | 11-13 | | |
| Aug. 6, 2008 | 11-13 | | |
| Aug. 7, 2008 | 11-13 | | |
| Aug. 8, 2008 | 10-12 | | |
| Aug. 9, 2008 | 10-12 | | |
| Aug. 10, 2008 | 10-12 | | |
| Aug. 11, 2008 | 10-12 | | |
| Aug. 12, 2008 | 9-11 | | |
| Aug. 13, 2008 | 9-11 | | |
| Aug. 14, 2008 | 9-11 | | |
| Aug. 15, 2008 | 9-11 | | |
| Aug. 16, 2008 | 8-10 | | |
| Aug. 17, 2008 | 8-10 | | |
| Aug. 18, 2008 | 8-10 | | |
| Aug. 19, 2008 | 8-10 | | |
| Aug. 20, 2008 | 7-9 | | |
| Aug. 21, 2008 | 7-9 | | |
| Aug. 22, 2008 | 7-9 | | |
| Aug. 23, 2008 | 7-9 | | |
| Aug. 24, 2008 | 6-8 | | |
| Aug. 25, 2008 | 6-8 | | |
| Aug. 26, 2008 | 6-8 | | |
| Aug. 27, 2008 | 6-8 | | |

TABLE 1-continued

Chesapeake Strain Yellow Perch Broodstock January Spawners
(Adjusted to Local Avg. Temps)
(From Chesapeake Normal March Spawners)

| Date | Temp Range | Temp Flow | Comments |
|---|---|---|---|
| Aug. 28, 2008 | 5-7 | | |
| Aug. 29, 2008 | 5-7 | | |
| Aug. 30, 2008 | 5-7 | | |
| Aug. 31, 2008 | 5-7 | | |
| Sep. 1, 2008 | 5-6 | | |
| Sep. 2, 2008 | 5-6 | | |
| Sep. 3, 2008 | 5-6 | | |
| Sep. 4, 2008 | 5-6 | | |
| Sep. 5, 2008 | 5-6 | | |
| Sep. 6, 2008 | 5-6 | | |
| Sep. 7, 2008 | 5-6 | | |
| Sep. 8, 2008 | 5-6 | | |
| Sep. 9, 2008 | 5-6 | | |
| Sep. 10, 2008 | 5-6 | | |
| Sep. 11, 2008 | 5-6 | | |
| Sep. 12, 2008 | 5-6 | | |
| Sep. 13, 2008 | 5-6 | | |
| Sep. 14, 2008 | 5-6 | | |
| Sep. 15, 2008 | 5-6 | | |
| Sep. 16, 2008 | 5-6 | | |
| Sep. 17, 2008 | 5-6 | | |
| Sep. 18, 2008 | 5-6 | | |
| Sep. 19, 2008 | 5-6 | | |
| Sep. 20, 2008 | 5-6 | | |
| Sep. 21, 2008 | 5-6 | | |
| Sep. 22, 2008 | 5-6 | | |
| Sep. 23, 2008 | 5-6 | | |
| Sep. 24, 2008 | 5-6 | | |
| Sep. 25, 2008 | 5-6 | | |
| Sep. 26, 2008 | 5-6 | | |
| Sep. 27, 2008 | 5-6 | | |
| Sep. 28, 2008 | 5-6 | | |
| Sep. 29, 2008 | 5-6 | | |
| Sep. 30, 2008 | 5-6 | | |
| Oct. 1, 2008 | 5-6 | | |
| Oct. 2, 2008 | 5-6 | | |
| Oct. 3, 2008 | 5-6 | | |
| Oct. 4, 2008 | 5-6 | | |
| Oct. 5, 2008 | 5-6 | | |
| Oct. 6, 2008 | 5-6 | | |
| Oct. 7, 2008 | 5-6 | | |
| Oct. 8, 2008 | 5-6 | | |
| Oct. 9, 2008 | 5-6 | | |
| Oct. 10, 2008 | 5-6 | | |
| Oct. 11, 2008 | 5-6 | | |
| Oct. 12, 2008 | 5-6 | | |
| Oct. 13, 2008 | 5-6 | | |
| Oct. 14, 2008 | 5-6 | | |
| Oct. 15, 2008 | 5-6 | | |
| Oct. 16, 2008 | 5-6 | | |
| Oct. 17, 2008 | 5-6 | | |
| Oct. 18, 2008 | 5-6 | | |
| Oct. 19, 2008 | 5-6 | | |
| Oct. 20, 2008 | 5-6 | | |
| Oct. 21, 2008 | 5-6 | | |
| Oct. 22, 2008 | 5-6 | | |
| Oct. 23, 2008 | 5-6 | | |
| Oct. 24, 2008 | 5-6 | | |
| Oct. 25, 2008 | 5-6 | | |
| Oct. 26, 2008 | 5-6 | | |
| Oct. 27, 2008 | 5-6 | | |
| Oct. 28, 2008 | 5-6 | | |
| Oct. 29, 2008 | 5-6 | | |
| Oct. 30, 2008 | 5-6 | | |
| Oct. 31, 2008 | 5-6 | | |
| Nov. 1, 2008 | 5-6 | | |
| Nov. 2, 2008 | 5-6 | | |
| Nov. 3, 2008 | 5-6 | | |
| Nov. 4, 2008 | 5-6 | | |
| Nov. 5, 2008 | 5-6 | | |
| Nov. 6, 2008 | 5-6 | | |
| Nov. 7, 2008 | 5-6 | | |
| Nov. 8, 2008 | 5-6 | | |
| Nov. 9, 2008 | 5-6 | | |
| Nov. 10, 2008 | 5-6 | | |
| Nov. 11, 2008 | 5-6 | | |
| Nov. 12, 2008 | 5-6 | | |
| Nov. 13, 2008 | 5-6 | | |
| Nov. 14, 2008 | 5-6 | | |
| Nov. 15, 2008 | 5-6 | | |
| Nov. 16, 2008 | 5-6 | | |
| Nov. 17, 2008 | 5-6 | | |
| Nov. 18, 2008 | 5-6 | | |
| Nov. 19, 2008 | 5-6 | | |
| Nov. 20, 2008 | 5-6 | | |
| Nov. 21, 2008 | 5-6 | | |
| Nov. 22, 2008 | 5-6 | | |
| Nov. 23, 2008 | 5-6 | | |
| Nov. 24, 2008 | 5-6 | | |
| Nov. 25, 2008 | 5-6 | | |
| Nov. 26, 2008 | 5-6 | | |
| Nov. 27, 2008 | 5-6 | | |
| Nov. 28, 2008 | 5-6 | | |
| Nov. 29, 2008 | 5-6 | | |
| Nov. 30, 2008 | 5-6 | | |
| Dec. 1, 2008 | 5-6 | | |
| Dec. 2, 2008 | 5-6 | | |
| Dec. 3, 2008 | 5-6 | | |
| Dec. 4, 2008 | 5-7 | | |
| Dec. 5, 2008 | 5-7 | | |
| Dec. 6, 2008 | 5-7 | | |
| Dec. 7, 2008 | 5-7 | | |
| Dec. 8, 2008 | 6-8 | | |
| Dec. 9, 2008 | 6-8 | | |
| Dec. 10, 2008 | 6-8 | | |
| Dec. 11, 2008 | 6-8 | | |
| Dec. 12, 2008 | 7-9 | | |
| Dec. 13, 2008 | 7-9 | | |
| Dec. 14, 2008 | 7-9 | | |
| Dec. 15, 2008 | 7-9 | | |
| Dec. 16, 2008 | 8-10 | | |
| Dec. 17, 2008 | 8-10 | | |
| Dec. 18, 2008 | 8-10 | | |
| Dec. 19, 2008 | 8-10 | | |
| Dec. 20, 2008 | 9-11 | | |
| Dec. 21, 2008 | 9-11 | | |
| Dec. 22, 2008 | 9-11 | | |
| Dec. 23, 2008 | 9-11 | | |
| Dec. 24, 2008 | 10-12 | | |
| Dec. 25, 2008 | 10-12 | | |
| Dec. 26, 2008 | 10-12 | | |
| Dec. 27, 2008 | 10-12 | | |
| Dec. 28, 2008 | 11-13 | | |
| Dec. 29, 2008 | 11-13 | | |
| Dec. 30, 2008 | 11-13 | | |
| Dec. 31, 2008 | 11-13 | | |
| Jan. 1, 2009 | 12-14 | | |
| Jan. 2, 2009 | 12-14 | | |
| Jan. 3, 2009 | 12-14 | | |
| Jan. 4, 2009 | 12-14 | | |
| Jan. 5, 2009 | 13-15 | | |
| Jan. 6, 2009 | 13-15 | | |
| Jan. 7, 2009 | 13-15 | | |
| Jan. 8, 2009 | 13-15 | | |
| Jan. 9, 2009 | 14-16 | | |
| Jan. 10, 2009 | 14-16 | | |
| Jan. 11, 2009 | 14-16 | | |
| Jan. 12, 2009 | 14-16 | | |
| Jan. 13, 2009 | 15-17 | | |
| Jan. 14, 2009 | 15-17 | | |
| Jan. 15, 2009 | 15-17 | | |
| Jan. 16, 2009 | 15-17 | | |
| Jan. 17, 2009 | 16-18 | | |
| Jan. 18, 2009 | 16-18 | | |

TABLE 1-continued

Chesapeake Strain Yellow Perch Broodstock January Spawners
(Adjusted to Local Avg. Temps)
(From Chesapeake Normal March Spawners)

| Date | Temp Range | Temp Flow | Comments |
|---|---|---|---|
| Jan. 19, 2009 | 16-18 | | |
| Jan. 20, 2009 | 16-18 | | |
| Jan. 21, 2009 | 17-19 | | |
| Jan. 22, 2009 | 17-19 | | |
| Jan. 23, 2009 | 17-19 | | |
| Jan. 24, 2009 | 17-19 | | |
| Jan. 25, 2009 | 18-20 | | |
| Jan. 26, 2009 | 18-20 | | |
| Jan. 27, 2009 | 18-20 | | |
| Jan. 28, 2009 | 18-20 | | |
| Jan. 29, 2009 | 19-21 | | |
| Jan. 30, 2009 | 19-21 | | |
| Jan. 31, 2009 | 19-21 | | |

Example 3

By manipulating water temperature and photoperiod as described above in Examples 1 and 2, a strain that normally spawns in April was manipulated to spawn in August, a strain that normally spawns in June was manipulated to spawn in October, a strain that normally spawns in March was manipulated to spawn in December, and a strain that normally spawns in March was manipulated to spawn in January.

Example 4

A first generation broodstock can also be shifted backward to produce an earlier spawning broodstock. In this example, the Sassafras River strain (normal March spawning) of yellow perch was used to develop a January out-of-cycle broodstock. The Sassafras River strain, which spawns in March, was selected for its biological characteristics and because its natural spawning time is in proximity to the desired out-of-cycle spawning time of January. Again, yearly local photoperiod and water temperature profiles were identified. In this example, rather than increasing the first summer, the first winter was decreased by 2 months to allow the new spring to begin in December rather than in February. The local temperature and photoperiod profiles were used from that point on, but they were shifted back 2 months. The first generation spawned in January.

The egg incubation and post-hatch water temperature schedule previously discussed was followed. The eggs from the first generation's January spawning were hatched out in January. The second generation was raised for 16 months at a constant temperature. Then, a second generation broodstock was selected. Again, yearly local photoperiod and water temperature profiles were identified. The development of an October spawning broodstock (3 months earlier than the first generation January spawning and 5 months earlier than the normal March spawning) was desired. The water temperatures and photoperiod were manipulated so that the second generation spawned in October. This was done by decreasing the winter by 5 months to allow the new spring to being in September rather than in February. The local temperature and photoperiod profiles were used from that point on, but they were shifted back 5 months from the normal, or 3 months from the January spawners. The second generation broodstock spawned in October.

Example 5

These are just some examples of phase shifting to develop out-of-cycle broodstocks. There may be a case where both the first summer and first winter lengths will need to be decreased (ex. Chesapeake March to out-of-cycle November). A Green Bay April to out-of-cycle October would require the first summer to be extended by 6 months. As mentioned earlier, success may decline the further away the geographic strain's spawning period is shifted from the normal spawning period.

The quality of the wild broodstock used to obtain the initial gametes is also a major factor in successful broodstock development. In general, a genetically diverse strain is better than a strain that is isolated and subject to inbreeding. However, the definition of genetically superior fish is varied depending on the needs of the producer. A producer that sells fish as stockers for fishing probably wants fish that grow large, survive well in local environmental conditions, are disease resistant, etc. A producer that raises fish to sell for food may only want fish that grow extremely fast so they can get their product to market rapidly.

Example 6

Using the previously mentioned methods to quantify the success of out-of-cycle broodstocks (GSI, proximate composition, fertility rate, hatching success, sac-fry survival, swim bladder inflation, etc.), several experiments are conducted to determine if improvements can be made to the broodstock development techniques.

Different treatments are performed to evaluate the effectiveness of different rearing methods. For example, using seasonal temperature and photoperiod regimes are compared to using a seasonal temperature regime only. Another treatment evaluates the success of broodstock that were reared in a recirculating aquaculture system (RAS). These fish are held at constant temperatures between about 20° C. and about 24° C. for their first 16 months before entering a seasonal temperature and photoperiod regime.

An experiment is run to compare the effects of increasing the time between a geographic strain's natural spawning time and the intended out-of-cycle spawning time. The North Carolina strain (normal March spawner) is used to produce March, May, July, and September spawning broodstocks. Evaluating the new broodstocks determines the degree to which the distance between normal and out-of-cycle spawning, within a geographic strain, affects broodstock development.

Genetically defining every possible geographic strain of yellow perch would benefit any perch production enterprise. The degree of genetic variability is tested to determine its effect on broodstock development. Some geographic strains of yellow perch have little genetic variability, and others have high variability. Comparing broodstocks with various genetic variability is expected to show a significant difference in spawning productivity. Genetic variability can also be the result of the number of females/males used for gamete collection. The variability of the offspring will be lower if only 5 females are collected in the wild as opposed to using the eggs from 20 females.

The degree of domestication of a broodstock should have an effect on out-of-cycle broodstock development/production. Trials are run to determine if an $F_1$ generation broodstock performs as well as an $F_2$ or $F_3$. Different generations are also tested by spawning in their normal cycle vs. a particular out-of-cycle time. Since domestication is an important factor in the production of other agricultural animals, yellow perch should also be affected.

Example 7

A broodstock can also be shifted forward to produce a later spawning broodstock. In this example, the Choptank River strain (normal March spawning) of yellow perch is used to develop a July out-of-cycle broodstock. The Choptank River strain, which spawns in March, is selected for its biological characteristics and because its natural spawning time is in proximity to the desired out-of-cycle spawning time of July. Again, yearly local photoperiod and water temperature profiles are identified. Eggs are fertilized in the field (Choptank River) and brought back to the lab. The egg incubation and post-hatch water temperature schedule previously discussed is followed. A yearly temperature and photoperiod profile is developed based on the geographic strain's local average conditions. Once the eggs hatch and normal summer temperatures are reached, those summer temperatures and photoperiods would usually be maintained until the autumn normally begins. However, the development of a July spawning broodstock (4 months later than normal) is desired. Therefore, the first summer after hatch is extended another 4 months. The summer water temperatures and photoperiods are maintained for an extra 4 months. In addition, the entire yearly local temperature and photoperiod profiles are shifted forward by 4 months. The new autumn then begins in December rather than August, and the new spring begins in June rather than February. This "tricks" the fish into thinking they are spawning in the spring, when in reality it is 4 months past normal spawning.

Example 8

Yellow perch spawn when the water temperature rises to about 10-12° C. in the spring. In the following example, a Sassafras River strain (normal March spawners) is used to develop a June spawning out-of-cycle broodstock. The Sassafras River strain, which spawns in March, is selected for its biological characteristics and because its natural spawning time is in close proximity to the desired out-of-cycle spawning time of June. Eggs are fertilized in the field (Sassafras River, Md.) and brought back to the lab. The egg incubation and post-hatch water temperature schedule previously discussed is followed. A yearly temperature and photoperiod profile is developed based on the geographic strain's local average conditions (Sassafras River, Md.). The photoperiod profile is simply the daily sunrise and sunset times for the strain's local area over a year. The water temperature profile is developed using average local water temperatures throughout the year. Once the eggs hatch and normal summer temperatures are reached, those summer temperatures and photoperiods would usually be maintained until the autumn normally begins. However, the development of a June spawning broodstock (3 months later than normal) is desired. Therefore, the first summer after hatch is extended another 3 months. The summer water temperatures and photoperiods are maintained for an extra 3 months. In addition, the entire yearly local temperature and photoperiod profiles are shifted forward by 3 months. The new autumn then begins in December rather than September, and the new spring begins in May rather than February. This "tricks" the fish into thinking they are spawning in the spring, when in reality it is 3 months past normal spawning.

The first generation that is manipulated to spawn in June is then used to develop a second generation broodstock that spawns in August. Eggs from the first generation (June spawners) are fertilized in the lab. The egg incubation and post-hatch water temperature schedule previously discussed is followed. A yearly temperature and photoperiod profiled is developed based on the geographic strain's local average conditions (Sassafras River, Md.). The photoperiod profile is simply the daily sunrise and sunset times for the strain's local area over a year. The water temperature profile is developed using average local water temperatures throughout the year. The development of an August spawning broodstock (2 months later than the June spawning from the first generation) is desired. Once the eggs hatch and normal summer temperatures are reached, those summer temperatures are extended for another 2 months. The summer water temperatures and photoperiods are maintained for an extra 2 months. In addition, the entire yearly local temperature and photoperiod profiles are shifted forward by 5 months. The new autumn then begins in February, rather than December, and the new spring beings in July rather than May. This "tricks" the fish into thinking they are spawning in the spring, when in reality it is 2 months past the first generational spawning time, and 5 months past the normal spawning time.

Example 9

In the following example, the Green Bay, Wis. strain (normal April spawners) is used to develop an August spawning out-of-cycle broodstock. The Green Bay strain is selected for its biological characteristics and because its natural spawning time is in proximity to the desired out-of-cycle spawning time of August. Eggs are fertilized in the field (Green Bay) and brought back to the lab. The egg incubation and post-hatch water temperature schedule previously discussed is followed. A yearly temperature and photoperiod profile is developed based on the geographic strain's local average conditions (Green Bay, Wis.). The photoperiod profile is simply the daily sunrise and sunset times for the strain's local area over a year. The water temperature profile is developed using average local water temperatures throughout the year. Once the eggs hatch and normal summer temperatures are reached, those summer temperatures and photoperiods would normally be maintained until September before the autumn begins. However, the development of an August spawning broodstock (4 months later than normal) is desired. So, rather than the autumn beginning in September, the first summer after hatch is extended another 4 months. The summer water temperatures and photoperiods are maintained for an extra 4 months. In addition, the entire yearly local temperature and photoperiod profiles are shifted forward by 4 months. The new autumn then begins in January rather than September, and the new spring begins in July rather than March. This "tricks" the fish into thinking they are spawning in the spring, when in reality it is 4 months past normal spawning. Further details are set forth in Table 2.

TABLE 2

Green Bay Strain Yellow Perch Broodstock August Spawners (Adjusted to Local Avg. Temps)
(From Green Bay Normal April Spawners)

| Date | Temp Range | Temp Flow | Comments |
|---|---|---|---|
| Apr. 21, 2007 | 10-12 | | ESTIMATED NORMAL SPAWN & EGG COLLECTION |
| Apr. 22, 2007 | 10-12 | | |
| Apr. 23, 2007 | 11-13 | | |

TABLE 2-continued

Green Bay Strain Yellow Perch Broodstock August
Spawners (Adjusted to Local Avg. Temps)
(From Green Bay Normal April Spawners)

| Date | Temp Range | Temp Flow | Comments |
|---|---|---|---|
| Apr. 24, 2007 | 11-13 | | |
| Apr. 25, 2007 | 12-14 | | |
| Apr. 26, 2007 | 12-14 | | |
| Apr. 27, 2007 | 13-15 | | |
| Apr. 28, 2007 | 13-15 | | |
| Apr. 29, 2007 | 14-16 | | |
| Apr. 30, 2007 | 14-16 | | |
| May 1, 2007 | 15-17 | | |
| May 2, 2007 | 15-17 | | |
| May 3, 2007 | 16-18 | | |
| May 4, 2007 | 16-18 | | ESTIMATED HATCH |
| May 5, 2007 | 17-19 | | |
| May 6, 2007 | 17-19 | | |
| May 7, 2007 | 18-20 | | |
| May 8, 2007 | 18-20 | | |
| May 9, 2007 | 19-21 | | |
| May 10, 2007 | 19-21 | | |
| May 11, 2007 | 20-22 | | |
| May 12, 2007 | 20-22 | | |
| May 13, 2007 | 20-22 | | |
| May 14, 2007 | 20-22 | | |
| May 15, 2007 | 20-22 | | |
| May 16, 2007 | 20-22 | | |
| May 17, 2007 | 20-22 | | |
| May 18, 2007 | 20-22 | | |
| May 19, 2007 | 20-22 | | |
| May 20, 2007 | 20-22 | | |
| May 21, 2007 | 20-22 | | |
| May 22, 2007 | 20-22 | | |
| May 23, 2007 | 20-22 | | |
| May 24, 2007 | 20-22 | | |
| May 25, 2007 | 20-22 | | |
| May 26, 2007 | 20-22 | | |
| May 27, 2007 | 20-22 | | |
| May 28, 2007 | 20-22 | | |
| May 29, 2007 | 20-22 | | |
| May 30, 2007 | 20-22 | | |
| May 31, 2007 | 20-22 | | |
| Jun. 1, 2007 | 20-22 | | |
| Jun. 2, 2007 | 20-22 | | |
| Jun. 3, 2007 | 20-22 | | |
| Jun. 4, 2007 | 20-22 | | |
| Jun. 5, 2007 | 20-22 | | |
| Jun. 6, 2007 | 20-22 | | |
| Jun. 7, 2007 | 20-22 | | |
| Jun. 8, 2007 | 20-22 | | |
| Jun. 9, 2007 | 20-22 | | |
| Jun. 10, 2007 | 20-22 | | |
| Jun. 11, 2007 | 20-22 | | |
| Jun. 12, 2007 | 20-22 | | |
| Jun. 13, 2007 | 20-22 | | |
| Jun. 14, 2007 | 20-22 | | |
| Jun. 15, 2007 | 20-22 | | |
| Jun. 16, 2007 | 20-22 | | |
| Jun. 17, 2007 | 20-22 | | |
| Jun. 18, 2007 | 20-22 | | |
| Jun. 19, 2007 | 20-22 | | |
| Jun. 20, 2007 | 20-22 | | |
| Jun. 21, 2007 | 20-22 | | |
| Jun. 22, 2007 | 20-22 | | |
| Jun. 23, 2007 | 20-22 | | |
| Jun. 24, 2007 | 20-22 | | |
| Jun. 25, 2007 | 20-22 | | |
| Jun. 26, 2007 | 20-22 | | |
| Jun. 27, 2007 | 20-22 | | |
| Jun. 28, 2007 | 20-22 | | |
| Jun. 29, 2007 | 20-22 | | |
| Jun. 30, 2007 | 20-22 | | |
| Jul. 1, 2007 | 20-22 | | |
| Jul. 2, 2007 | 20-22 | | |
| Jul. 3, 2007 | 20-22 | | |
| Jul. 4, 2007 | 20-22 | | |
| Jul. 5, 2007 | 20-22 | | |
| Jul. 6, 2007 | 20-22 | | |
| Jul. 7, 2007 | 20-22 | | |
| Jul. 8, 2007 | 20-22 | | |
| Jul. 9, 2007 | 20-22 | | |
| Jul. 10, 2007 | 20-22 | | |
| Jul. 11, 2007 | 20-22 | | |
| Jul. 12, 2007 | 20-22 | | |
| Jul. 13, 2007 | 20-22 | | |
| Jul. 14, 2007 | 20-22 | | |
| Jul. 15, 2007 | 20-22 | | |
| Jul. 16, 2007 | 20-22 | | |
| Jul. 17, 2007 | 20-22 | | |
| Jul. 18, 2007 | 20-22 | | |
| Jul. 19, 2007 | 20-22 | | |
| Jul. 20, 2007 | 20-22 | | |
| Jul. 21, 2007 | 20-22 | | |
| Jul. 22, 2007 | 20-22 | | |
| Jul. 23, 2007 | 20-22 | | |
| Jul. 24, 2007 | 20-22 | | |
| Jul. 25, 2007 | 20-22 | | |
| Jul. 26, 2007 | 20-22 | | |
| Jul. 27, 2007 | 20-22 | | |
| Jul. 28, 2007 | 20-22 | | |
| Jul. 29, 2007 | 20-22 | | |
| Jul. 30, 2007 | 20-22 | | |
| Jul. 31, 2007 | 20-22 | | |
| Aug. 1, 2007 | 20-22 | | |
| Aug. 2, 2007 | 20-22 | | |
| Aug. 3, 2007 | 20-22 | | |
| Aug. 4, 2007 | 20-22 | | |
| Aug. 5, 2007 | 20-22 | | |
| Aug. 6, 2007 | 20-22 | | |
| Aug. 7, 2007 | 20-22 | | |
| Aug. 8, 2007 | 20-22 | | |
| Aug. 9, 2007 | 20-22 | | |
| Aug. 10, 2007 | 20-22 | | |
| Aug. 11, 2007 | 20-22 | | |
| Aug. 12, 2007 | 20-22 | | |
| Aug. 13, 2007 | 20-22 | | |
| Aug. 14, 2007 | 20-22 | | |
| Aug. 15, 2007 | 20-22 | | |
| Aug. 16, 2007 | 20-22 | | |
| Aug. 17, 2007 | 20-22 | | |
| Aug. 18, 2007 | 20-22 | | |
| Aug. 19, 2007 | 20-22 | | |
| Aug. 20, 2007 | 20-22 | | |
| Aug. 21, 2007 | 20-22 | | |
| Aug. 22, 2007 | 20-22 | | |
| Aug. 23, 2007 | 20-22 | | |
| Aug. 24, 2007 | 20-22 | | |
| Aug. 25, 2007 | 20-22 | | |
| Aug. 26, 2007 | 20-22 | | |
| Aug. 27, 2007 | 20-22 | | |
| Aug. 28, 2007 | 20-22 | | |
| Aug. 29, 2007 | 20-22 | | |
| Aug. 30, 2007 | 20-22 | | |
| Aug. 31, 2007 | 20-22 | | |
| Sep. 1, 2007 | 20-22 | | |
| Sep. 2, 2007 | 20-22 | | |
| Sep. 3, 2007 | 20-22 | | |
| Sep. 4, 2007 | 20-22 | | |
| Sep. 5, 2007 | 20-22 | | |
| Sep. 6, 2007 | 20-22 | | |
| Sep. 7, 2007 | 20-22 | | |
| Sep. 8, 2007 | 20-22 | | |
| Sep. 9, 2007 | 20-22 | | |
| Sep. 10, 2007 | 20-22 | | |
| Sep. 11, 2007 | 20-22 | | |
| Sep. 12, 2007 | 20-22 | | |
| Sep. 13, 2007 | 20-22 | | |
| Sep. 14, 2007 | 20-22 | | |

TABLE 2-continued

Green Bay Strain Yellow Perch Broodstock August
Spawners (Adjusted to Local Avg. Temps)
(From Green Bay Normal April Spawners)

| Date | Temp Range | Temp Flow | Comments |
|---|---|---|---|
| Sep. 15, 2007 | 20-22 | | The 1st summer is extended 4 more months to shift into new August out-of-cycle |
| Sep. 16, 2007 | 20-22 | | |
| Sep. 17, 2007 | 20-22 | | |
| Sep. 18, 2007 | 20-22 | | |
| Sep. 19, 2007 | 20-22 | | |
| Sep. 20, 2007 | 20-22 | | |
| Sep. 21, 2007 | 20-22 | | |
| Sep. 22, 2007 | 20-22 | | |
| Sep. 23, 2007 | 20-22 | | |
| Sep. 24, 2007 | 20-22 | | |
| Sep. 25, 2007 | 20-22 | | |
| Sep. 26, 2007 | 20-22 | | |
| Sep. 27, 2007 | 20-22 | | |
| Sep. 28, 2007 | 20-22 | | |
| Sep. 29, 2007 | 20-22 | | |
| Sep. 30, 2007 | 20-22 | | |
| Oct. 1, 2007 | 20-22 | | |
| Oct. 2, 2007 | 20-22 | | |
| Oct. 3, 2007 | 20-22 | | |
| Oct. 4, 2007 | 20-22 | | |
| Oct. 5, 2007 | 20-22 | | |
| Oct. 6, 2007 | 20-22 | | |
| Oct. 7, 2007 | 20-22 | | |
| Oct. 8, 2007 | 20-22 | | |
| Oct. 9, 2007 | 20-22 | | |
| Oct. 10, 2007 | 20-22 | | |
| Oct. 11, 2007 | 20-22 | | |
| Oct. 12, 2007 | 20-22 | | |
| Oct. 13, 2007 | 20-22 | | |
| Oct. 14, 2007 | 20-22 | | |
| Oct. 15, 2007 | 20-22 | | |
| Oct. 16, 2007 | 20-22 | | |
| Oct. 17, 2007 | 20-22 | | |
| Oct. 18, 2007 | 20-22 | | |
| Oct. 19, 2007 | 20-22 | | |
| Oct. 20, 2007 | 20-22 | | |
| Oct. 21, 2007 | 20-22 | | |
| Oct. 22, 2007 | 20-22 | | |
| Oct. 23, 2007 | 20-22 | | |
| Oct. 24, 2007 | 20-22 | | |
| Oct. 25, 2007 | 20-22 | | |
| Oct. 26, 2007 | 20-22 | | |
| Oct. 27, 2007 | 20-22 | | |
| Oct. 28, 2007 | 20-22 | | |
| Oct. 29, 2007 | 20-22 | | |
| Oct. 30, 2007 | 20-22 | | |
| Oct. 31, 2007 | 20-22 | | |
| Nov. 1, 2007 | 20-22 | | |
| Nov. 2, 2007 | 20-22 | | |
| Nov. 3, 2007 | 20-22 | | |
| Nov. 4, 2007 | 20-22 | | |
| Nov. 5, 2007 | 20-22 | | |
| Nov. 6, 2007 | 20-22 | | |
| Nov. 7, 2007 | 20-22 | | |
| Nov. 8, 2007 | 20-22 | | |
| Nov. 9, 2007 | 20-22 | | |
| Nov. 10, 2007 | 20-22 | | |
| Nov. 11, 2007 | 20-22 | | |
| Nov. 12, 2007 | 20-22 | | |
| Nov. 13, 2007 | 20-22 | | |
| Nov. 14, 2007 | 20-22 | | |
| Nov. 15, 2007 | 20-22 | | |
| Nov. 16, 2007 | 20-22 | | |
| Nov. 17, 2007 | 20-22 | | |
| Nov. 18, 2007 | 20-22 | | |
| Nov. 19, 2007 | 20-22 | | |
| Nov. 20, 2007 | 20-22 | | |
| Nov. 21, 2007 | 20-22 | | |
| Nov. 22, 2007 | 20-22 | | |
| Nov. 23, 2007 | 20-22 | | |
| Nov. 24, 2007 | 20-22 | | |
| Nov. 25, 2007 | 20-22 | | |
| Nov. 26, 2007 | 20-22 | | |
| Nov. 27, 2007 | 20-22 | | |
| Nov. 28, 2007 | 20-22 | | |
| Nov. 29, 2007 | 20-22 | | |
| Nov. 30, 2007 | 20-22 | | |
| Dec. 1, 2007 | 20-22 | | |
| Dec. 2, 2007 | 20-22 | | |
| Dec. 3, 2007 | 20-22 | | |
| Dec. 4, 2007 | 20-22 | | |
| Dec. 5, 2007 | 20-22 | | |
| Dec. 6, 2007 | 20-22 | | |
| Dec. 7, 2007 | 20-22 | | |
| Dec. 8, 2007 | 20-22 | | |
| Dec. 9, 2007 | 20-22 | | |
| Dec. 10, 2007 | 20-22 | | |
| Dec. 11, 2007 | 20-22 | | |
| Dec. 12, 2007 | 20-22 | | |
| Dec. 13, 2007 | 20-22 | | |
| Dec. 14, 2007 | 20-22 | | |
| Dec. 15, 2007 | 20-22 | | |
| Dec. 16, 2007 | 20-22 | | |
| Dec. 17, 2007 | 20-22 | | |
| Dec. 18, 2007 | 20-22 | | |
| Dec. 19, 2007 | 20-22 | | |
| Dec. 20, 2007 | 20-22 | | |
| Dec. 21, 2007 | 20-22 | | |
| Dec. 22, 2007 | 20-22 | | |
| Dec. 23, 2007 | 20-22 | | |
| Dec. 24, 2007 | 20-22 | | |
| Dec. 25, 2007 | 20-22 | | |
| Dec. 26, 2007 | 20-22 | | |
| Dec. 27, 2007 | 20-22 | | |
| Dec. 28, 2007 | 20-22 | | |
| Dec. 29, 2007 | 20-22 | | |
| Dec. 30, 2007 | 20-22 | | |
| Dec. 31, 2007 | 20-22 | | |
| Jan. 1, 2008 | 20-22 | | |
| Jan. 2, 2008 | 20-22 | | |
| Jan. 3, 2008 | 20-22 | | |
| Jan. 4, 2008 | 20-22 | | |
| Jan. 5, 2008 | 20-22 | | |
| Jan. 6, 2008 | 20-22 | | |
| Jan. 7, 2008 | 20-22 | | |
| Jan. 8, 2008 | 20-22 | | |
| Jan. 9, 2008 | 19-21 | | |
| Jan. 10, 2008 | 19-21 | | |
| Jan. 11, 2008 | 19-21 | | |
| Jan. 12, 2008 | 18-20 | | |
| Jan. 13, 2008 | 18-20 | | |
| Jan. 14, 2008 | 18-20 | | |
| Jan. 15, 2008 | 17-19 | | |
| Jan. 16, 2008 | 17-19 | | |
| Jan. 17, 2008 | 17-19 | | |
| Jan. 18, 2008 | 16-18 | | |
| Jan. 19, 2008 | 16-18 | | |
| Jan. 20, 2008 | 16-18 | | |
| Jan. 21, 2008 | 15-17 | | |
| Jan. 22, 2008 | 15-17 | | |
| Jan. 23, 2008 | 15-17 | | |
| Jan. 24, 2008 | 14-16 | | |
| Jan. 25, 2008 | 14-16 | | |
| Jan. 26, 2008 | 14-16 | | |
| Jan. 27, 2008 | 13-15 | | |
| Jan. 28, 2008 | 13-15 | | |
| Jan. 29, 2008 | 13-15 | | |
| Jan. 30, 2008 | 12-14 | | |
| Jan. 31, 2008 | 12-14 | | |
| Feb. 1, 2008 | 12-14 | | |
| Feb. 2, 2008 | 11-13 | | |
| Feb. 3, 2008 | 11-13 | | |
| Feb. 4, 2008 | 11-13 | | |
| Feb. 5, 2008 | 10-12 | | |

TABLE 2-continued

Green Bay Strain Yellow Perch Broodstock August
Spawners (Adjusted to Local Avg. Temps)
(From Green Bay Normal April Spawners)

| Date | Temp Range | Temp Flow | Comments |
|---|---|---|---|
| Feb. 6, 2008 | 10-12 | | |
| Feb. 7, 2008 | 10-12 | | |
| Feb. 8, 2008 | 9-11 | | |
| Feb. 9, 2008 | 9-11 | | |
| Feb. 10, 2008 | 9-11 | | |
| Feb. 11, 2008 | 8-10 | | |
| Feb. 12, 2008 | 8-10 | | |
| Feb. 13, 2008 | 8-10 | | |
| Feb. 14, 2008 | 7-9 | | |
| Feb. 15, 2008 | 7-9 | | |
| Feb. 16, 2008 | 7-9 | | |
| Feb. 17, 2008 | 6-8 | | |
| Feb. 18, 2008 | 6-8 | | |
| Feb. 19, 2008 | 6-8 | | |
| Feb. 20, 2008 | 5-7 | | |
| Feb. 21, 2008 | 5-7 | | |
| Feb. 22, 2008 | 5-7 | | |
| Feb. 23, 2008 | 5-7 | | |
| Feb. 24, 2008 | 5-7 | | |
| Feb. 25, 2008 | 5-7 | | |
| Feb. 26, 2008 | 5-7 | | |
| Feb. 27, 2008 | 5-7 | | |
| Feb. 28, 2008 | 5-7 | | |
| Feb. 29, 2008 | 5-7 | | |
| Mar. 1, 2008 | 5-7 | | |
| Mar. 2, 2008 | 5-7 | | |
| Mar. 3, 2008 | 5-7 | | |
| Mar. 4, 2008 | 5-7 | | |
| Mar. 5, 2008 | 5-7 | | |
| Mar. 6, 2008 | 5-7 | | |
| Mar. 7, 2008 | 5-7 | | |
| Mar. 8, 2008 | 5-7 | | |
| Mar. 9, 2008 | 5-7 | | |
| Mar. 10, 2008 | 5-7 | | |
| Mar. 11, 2008 | 5-7 | | |
| Mar. 12, 2008 | 5-7 | | |
| Mar. 13, 2008 | 5-7 | | |
| Mar. 14, 2008 | 5-7 | | |
| Mar. 15, 2008 | 5-7 | | |
| Mar. 16, 2008 | 5-7 | | |
| Mar. 17, 2008 | 5-7 | | |
| Mar. 18, 2008 | 5-7 | | |
| Mar. 19, 2008 | 5-7 | | |
| Mar. 20, 2008 | 5-7 | | |
| Mar. 21, 2008 | 5-7 | | |
| Mar. 22, 2008 | 5-7 | | |
| Mar. 23, 2008 | 5-7 | | |
| Mar. 24, 2008 | 5-7 | | |
| Mar. 25, 2008 | 5-7 | | |
| Mar. 26, 2008 | 5-7 | | |
| Mar. 27, 2008 | 5-7 | | |
| Mar. 28, 2008 | 5-7 | | |
| Mar. 29, 2008 | 5-7 | | |
| Mar. 30, 2008 | 5-7 | | |
| Mar. 31, 2008 | 5-7 | | |
| Apr. 1, 2008 | 5-7 | | |
| Apr. 2, 2008 | 5-7 | | |
| Apr. 3, 2008 | 5-7 | | |
| Apr. 4, 2008 | 5-7 | | |
| Apr. 5, 2008 | 5-7 | | |
| Apr. 6, 2008 | 5-7 | | |
| Apr. 7, 2008 | 5-7 | | |
| Apr. 8, 2008 | 5-7 | | |
| Apr. 9, 2008 | 5-7 | | |
| Apr. 10, 2008 | 5-7 | | |
| Apr. 11, 2008 | 5-7 | | |
| Apr. 12, 2008 | 5-7 | | |
| Apr. 13, 2008 | 5-7 | | |
| Apr. 14, 2008 | 5-7 | | |
| Apr. 15, 2008 | 5-7 | | |
| Apr. 16, 2008 | 5-7 | | |
| Apr. 17, 2008 | 5-7 | | |
| Apr. 18, 2008 | 5-7 | | |
| Apr. 19, 2008 | 5-7 | | |
| Apr. 20, 2008 | 5-7 | | |
| Apr. 21, 2008 | 5-7 | | |
| Apr. 22, 2008 | 5-7 | | |
| Apr. 23, 2008 | 5-7 | | |
| Apr. 24, 2008 | 5-7 | | |
| Apr. 25, 2008 | 5-7 | | |
| Apr. 26, 2008 | 5-7 | | |
| Apr. 27, 2008 | 5-7 | | |
| Apr. 28, 2008 | 5-7 | | |
| Apr. 29, 2008 | 5-7 | | |
| Apr. 30, 2008 | 5-7 | | |
| May 1, 2008 | 5-7 | | |
| May 2, 2008 | 5-7 | | |
| May 3, 2008 | 5-7 | | |
| May 4, 2008 | 5-7 | | |
| May 5, 2008 | 5-7 | | |
| May 6, 2008 | 5-7 | | |
| May 7, 2008 | 5-7 | | |
| May 8, 2008 | 5-7 | | |
| May 9, 2008 | 5-7 | | |
| May 10, 2008 | 5-7 | | |
| May 11, 2008 | 5-7 | | |
| May 12, 2008 | 5-7 | | |
| May 13, 2008 | 5-7 | | |
| May 14, 2008 | 5-7 | | |
| May 15, 2008 | 5-7 | | |
| May 16, 2008 | 5-7 | | |
| May 17, 2008 | 5-7 | | |
| May 18, 2008 | 5-7 | | |
| May 19, 2008 | 5-7 | | |
| May 20, 2008 | 5-7 | | |
| May 21, 2008 | 5-7 | | |
| May 22, 2008 | 5-7 | | |
| May 23, 2008 | 5-7 | | |
| May 24, 2008 | 5-7 | | |
| May 25, 2008 | 5-7 | | |
| May 26, 2008 | 5-7 | | |
| May 27, 2008 | 5-7 | | |
| May 28, 2008 | 5-7 | | |
| May 29, 2008 | 5-7 | | |
| May 30, 2008 | 5-7 | | |
| May 31, 2008 | 5-7 | | |
| Jun. 1, 2008 | 5-7 | | |
| Jun. 2, 2008 | 5-7 | | |
| Jun. 3, 2008 | 5-7 | | |
| Jun. 4, 2008 | 5-7 | | |
| Jun. 5, 2008 | 5-7 | | |
| Jun. 6, 2008 | 5-7 | | |
| Jun. 7, 2008 | 5-7 | | |
| Jun. 8, 2008 | 5-7 | | |
| Jun. 9, 2008 | 5-7 | | |
| Jun. 10, 2008 | 5-7 | | |
| Jun. 11, 2008 | 5-7 | | |
| Jun. 12, 2008 | 5-7 | | |
| Jun. 13, 2008 | 5-7 | | |
| Jun. 14, 2008 | 5-7 | | |
| Jun. 15, 2008 | 5-7 | | |
| Jun. 16, 2008 | 5-7 | | |
| Jun. 17, 2008 | 5-7 | | |
| Jun. 18, 2008 | 5-7 | | |
| Jun. 19, 2008 | 5-7 | | |
| Jun. 20, 2008 | 5-7 | | |
| Jun. 21, 2008 | 5-7 | | |
| Jun. 22, 2008 | 5-7 | | |
| Jun. 23, 2008 | 5-7 | | |
| Jun. 24, 2008 | 5-7 | | |
| Jun. 25, 2008 | 5-7 | | |
| Jun. 26, 2008 | 5-7 | | |
| Jun. 27, 2008 | 5-7 | | |
| Jun. 28, 2008 | 5-7 | | |

TABLE 2-continued

Green Bay Strain Yellow Perch Broodstock August
Spawners (Adjusted to Local Avg. Temps)
(From Green Bay Normal April Spawners)

| Date | Temp Range | Temp Flow | Comments |
|---|---|---|---|
| Jun. 29, 2008 | 5-7 | | |
| Jun. 30, 2008 | 5-7 | | |
| Jul. 1, 2008 | 5-7 | | |
| Jul. 2, 2008 | 5-7 | | |
| Jul. 3, 2008 | 5-7 | | |
| Jul. 4, 2008 | 5-7 | | |
| Jul. 5, 2008 | 5-7 | | |
| Jul. 6, 2008 | 5-7 | | |
| Jul. 7, 2008 | 5-7 | | |
| Jul. 8, 2008 | 5-7 | | |
| Jul. 9, 2008 | 5-7 | | |
| Jul. 10, 2008 | 5-7 | | |
| Jul. 11, 2008 | 5-7 | | |
| Jul. 12, 2008 | 5-7 | | |
| Jul. 13, 2008 | 5-7 | | |
| Jul. 14, 2008 | 5-7 | | |
| Jul. 15, 2008 | 5-7 | | |
| Jul. 16, 2008 | 5-7 | | |
| Jul. 17, 2008 | 5-7 | | |
| Jul. 18, 2008 | 5-7 | | |
| Jul. 19, 2008 | 5-7 | | |
| Jul. 20, 2008 | 5-7 | | |
| Jul. 21, 2008 | 5-7 | | |
| Jul. 22, 2008 | 6-8 | | |
| Jul. 23, 2008 | 6-8 | | |
| Jul. 24, 2008 | 6-8 | | |
| Jul. 25, 2008 | 7-9 | | |
| Jul. 26, 2008 | 7-9 | | |
| Jul. 27, 2008 | 7-9 | | |
| Jul. 28, 2008 | 8-10 | | |
| Jul. 29, 2008 | 8-10 | | |
| Jul. 30, 2008 | 8-10 | | |
| Jul. 31, 2008 | 9-11 | | |
| Aug. 1, 2008 | 9-11 | | |
| Aug. 2, 2008 | 9-11 | | |
| Aug. 3, 2008 | 10-12 | | |
| Aug. 4, 2008 | 10-12 | | |
| Aug. 5, 2008 | 10-12 | | |
| Aug. 6, 2008 | 11-13 | | |
| Aug. 7, 2008 | 11-13 | | |
| Aug. 8, 2008 | 11-13 | | |
| Aug. 9, 2008 | 12-14 | | |
| Aug. 10, 2008 | 12-14 | | |
| Aug. 11, 2008 | 12-14 | | |
| Aug. 12, 2008 | 13-15 | | |
| Aug. 13, 2008 | 13-15 | | |
| Aug. 14, 2008 | 13-15 | | |
| Aug. 15, 2008 | 14-16 | | |
| Aug. 16, 2008 | 14-16 | | |
| Aug. 17, 2008 | 14-16 | | |
| Aug. 18, 2008 | 15-17 | | |
| Aug. 19, 2008 | 15-17 | | |
| Aug. 20, 2008 | 15-17 | | |
| Aug. 21, 2008 | 16-18 | | |
| Aug. 22, 2008 | 16-18 | | |
| Aug. 23, 2008 | 16-18 | | |
| Aug. 24, 2008 | 17-19 | | |
| Aug. 25, 2008 | 17-19 | | |
| Aug. 26, 2008 | 17-19 | | |
| Aug. 27, 2008 | 18-20 | | |
| Aug. 28, 2008 | 18-20 | | |
| Aug. 29, 2008 | 18-20 | | |
| Aug. 30, 2008 | 19-21 | | |
| Aug. 31, 2008 | 19-21 | | |
| Sep. 1, 2008 | 19-21 | | |
| Sep. 2, 2008 | 20-22 | | |
| Sep. 3, 2008 | 20-22 | | |
| Sep. 4, 2008 | 20-22 | | |
| Sep. 5, 2008 | 20-22 | | |
| Sep. 6, 2008 | 20-22 | | |
| Sep. 7, 2008 | 20-22 | | |
| Sep. 8, 2008 | 20-22 | | |
| Sep. 9, 2008 | 20-22 | | |
| Sep. 10, 2008 | 20-22 | | |
| Sep. 11, 2008 | 20-22 | | |
| Sep. 12, 2008 | 20-22 | | |
| Sep. 13, 2008 | 20-22 | | |
| Sep. 14, 2008 | 20-22 | | |
| Sep. 15, 2008 | 20-22 | | |
| Sep. 16, 2008 | 20-22 | | |
| Sep. 17, 2008 | 20-22 | | |
| Sep. 18, 2008 | 20-22 | | |
| Sep. 19, 2008 | 20-22 | | |
| Sep. 20, 2008 | 20-22 | | |
| Sep. 21, 2008 | 20-22 | | |
| Sep. 22, 2008 | 20-22 | | |
| Sep. 23, 2008 | 20-22 | | |
| Sep. 24, 2008 | 20-22 | | |
| Sep. 25, 2008 | 20-22 | | |
| Sep. 26, 2008 | 20-22 | | |
| Sep. 27, 2008 | 20-22 | | |
| Sep. 28, 2008 | 20-22 | | |
| Sep. 29, 2008 | 20-22 | | |
| Sep. 30, 2008 | 20-22 | | |
| Oct. 1, 2008 | 20-22 | | |
| Oct. 2, 2008 | 20-22 | | |
| Oct. 3, 2008 | 20-22 | | |
| Oct. 4, 2008 | 20-22 | | |
| Oct. 5, 2008 | 20-22 | | |
| Oct. 6, 2008 | 20-22 | | |
| Oct. 7, 2008 | 20-22 | | |
| Oct. 8, 2008 | 20-22 | | |
| Oct. 9, 2008 | 20-22 | | |
| Oct. 10, 2008 | 20-22 | | |
| Oct. 11, 2008 | 20-22 | | |
| Oct. 12, 2008 | 20-22 | | |
| Oct. 13, 2008 | 20-22 | | |
| Oct. 14, 2008 | 20-22 | | |
| Oct. 15, 2008 | 20-22 | | |
| Oct. 16, 2008 | 20-22 | | |
| Oct. 17, 2008 | 20-22 | | |
| Oct. 18, 2008 | 20-22 | | |
| Oct. 19, 2008 | 20-22 | | |
| Oct. 20, 2008 | 20-22 | | |
| Oct. 21, 2008 | 20-22 | | |
| Oct. 22, 2008 | 20-22 | | |
| Oct. 23, 2008 | 20-22 | | |
| Oct. 24, 2008 | 20-22 | | |
| Oct. 25, 2008 | 20-22 | | |
| Oct. 26, 2008 | 20-22 | | |
| Oct. 27, 2008 | 20-22 | | |
| Oct. 28, 2008 | 20-22 | | |
| Oct. 29, 2008 | 20-22 | | |
| Oct. 30, 2008 | 20-22 | | |
| Oct. 31, 2008 | 20-22 | | |
| Nov. 1, 2008 | 20-22 | | |
| Nov. 2, 2008 | 20-22 | | |
| Nov. 3, 2008 | 20-22 | | |
| Nov. 4, 2008 | 20-22 | | |
| Nov. 5, 2008 | 20-22 | | |
| Nov. 6, 2008 | 20-22 | | |
| Nov. 7, 2008 | 20-22 | | |
| Nov. 8, 2008 | 20-22 | | |
| Nov. 9, 2008 | 20-22 | | |
| Nov. 10, 2008 | 20-22 | | |
| Nov. 11, 2008 | 20-22 | | |
| Nov. 12, 2008 | 20-22 | | |
| Nov. 13, 2008 | 20-22 | | |
| Nov. 14, 2008 | 20-22 | | |
| Nov. 15, 2008 | 20-22 | | |
| Nov. 16, 2008 | 20-22 | | |
| Nov. 17, 2008 | 20-22 | | |
| Nov. 18, 2008 | 20-22 | | |
| Nov. 19, 2008 | 20-22 | | |

TABLE 2-continued

Green Bay Strain Yellow Perch Broodstock August
Spawners (Adjusted to Local Avg. Temps)
(From Green Bay Normal April Spawners)

| Date | Temp Range | Temp Flow | Comments |
|---|---|---|---|
| Nov. 20, 2008 | 20-22 | | |
| Nov. 21, 2008 | 20-22 | | |
| Nov. 22, 2008 | 20-22 | | |
| Nov. 23, 2008 | 20-22 | | |
| Nov. 24, 2008 | 20-22 | | |
| Nov. 25, 2008 | 20-22 | | |
| Nov. 26, 2008 | 20-22 | | |
| Nov. 27, 2008 | 20-22 | | |
| Nov. 28, 2008 | 20-22 | | |
| Nov. 29, 2008 | 20-22 | | |
| Nov. 30, 2008 | 20-22 | | |
| Dec. 1, 2008 | 20-22 | | |
| Dec. 2, 2008 | 20-22 | | |
| Dec. 3, 2008 | 20-22 | | |
| Dec. 4, 2008 | 20-22 | | |
| Dec. 5, 2008 | 20-22 | | |
| Dec. 6, 2008 | 20-22 | | |
| Dec. 7, 2008 | 20-22 | | |
| Dec. 8, 2008 | 20-22 | | |
| Dec. 9, 2008 | 20-22 | | |
| Dec. 10, 2008 | 20-22 | | |
| Dec. 11, 2008 | 20-22 | | |
| Dec. 12, 2008 | 20-22 | | |
| Dec. 13, 2008 | 20-22 | | |
| Dec. 14, 2008 | 20-22 | | |
| Dec. 15, 2008 | 20-22 | | |
| Dec. 16, 2008 | 20-22 | | |
| Dec. 17, 2008 | 20-22 | | |
| Dec. 18, 2008 | 20-22 | | |
| Dec. 19, 2008 | 20-22 | | |
| Dec. 20, 2008 | 20-22 | | |
| Dec. 21, 2008 | 20-22 | | |
| Dec. 22, 2008 | 20-22 | | |
| Dec. 23, 2008 | 20-22 | | |
| Dec. 24, 2008 | 20-22 | | |
| Dec. 25, 2008 | 20-22 | | |
| Dec. 26, 2008 | 20-22 | | |
| Dec. 27, 2008 | 20-22 | | |
| Dec. 28, 2008 | 20-22 | | |
| Dec. 29, 2008 | 20-22 | | |
| Dec. 30, 2008 | 20-22 | | |
| Dec. 31, 2008 | 20-22 | | |
| Jan. 1, 2009 | 20-22 | | |
| Jan. 2, 2009 | 20-22 | | |
| Jan. 3, 2009 | 20-22 | | |
| Jan. 4, 2009 | 20-22 | | |
| Jan. 5, 2009 | 20-22 | | |
| Jan. 6, 2009 | 20-22 | | |
| Jan. 7, 2009 | 20-22 | | |
| Jan. 8, 2009 | 20-22 | | |
| Jan. 9, 2009 | 19-21 | | |
| Jan. 10, 2009 | 19-21 | | |
| Jan. 11, 2009 | 19-21 | | |
| Jan. 12, 2009 | 18-20 | | |
| Jan. 13, 2009 | 18-20 | | |
| Jan. 14, 2009 | 18-20 | | |
| Jan. 15, 2009 | 17-19 | | |
| Jan. 16, 2009 | 17-19 | | |
| Jan. 17, 2009 | 17-19 | | |
| Jan. 18, 2009 | 16-18 | | |
| Jan. 19, 2009 | 16-18 | | |
| Jan. 20, 2009 | 16-18 | | |
| Jan. 21, 2009 | 15-17 | | |
| Jan. 22, 2009 | 15-17 | | |
| Jan. 23, 2009 | 15-17 | | |
| Jan. 24, 2009 | 14-16 | | |
| Jan. 25, 2009 | 14-16 | | |
| Jan. 26, 2009 | 14-16 | | |
| Jan. 27, 2009 | 13-15 | | |
| Jan. 28, 2009 | 13-15 | | |
| Jan. 29, 2009 | 13-15 | | |
| Jan. 30, 2009 | 12-14 | | |
| Jan. 31, 2009 | 12-14 | | |

What is claimed is:

1. A method of manipulating a spawning cycle of perch across multiple generations, the method comprising:
   identifying a first out-of-cycle spawning period for perch;
   selecting a geographic strain of perch having a natural spawning period different from the first out-of-cycle spawning period;
   developing a first generation broodstock from the geographic strain, wherein the broodstock's natural spawning period has been shifted to the first out-of-cycle spawning period using at least one of temperature and photoperiod manipulation;
   dividing the first generation broodstock into a first group and a second group;
   identifying a second out-of-cycle spawning period different from the natural spawning period and the first out-of-cycle spawning period;
   developing a second generation broodstock from the first group within the first generation broodstock, wherein the second generation broodstock's spawning period has been shifted from the first out-of-cycle spawning period to the second out-of-cycle spawning period using at least one of temperature and photoperiod manipulation; and
   developing at least one additional generation of broodstock from the second group within the first generation broodstock, wherein the additional generation of broodstock spawns during the first out-of-cycle spawning period.

2. The method of claim 1, wherein the temperature is manipulated by:
   identifying a local temperature profile for the geographic strain of perch;
   maintaining winter temperatures for about 100 to about 180 days;
   increasing temperature by about 1° C. every 2 to 4 days for spring, wherein spring lasts for about 56 to about 60 days;
   extending or reducing the length of the summer season to achieve the first out-of-cycle spawning period;
   decreasing temperature by about 1° C. every 2 to 4 days for autumn, wherein autumn lasts for about 42 to about 60 days.

3. The method of claim 1, wherein the photoperiod is manipulated by:
   identifying a local photoperiod profile for the geographic strain of perch;
   following a regional seasonal cycle of sunrise and sunset times to correspond with the season;
   extending or reducing the length of the summer season to achieve the first out-of-cycle spawning period.

4. The method of claim 1, wherein the geographic strain of perch has a natural spawning period within a 4 month proximity to the first out-of-cycle spawning period.

5. The method of claim 1, wherein the geographic strain of perch has a natural spawning period within a 2 month proximity to the first out-of-cycle spawning period.

6. The method of claim 1, wherein the geographic strain of perch is selected from a United States East Coast yellow perch population.

7. The method of claim 6, wherein the geographic strain of perch is selected from the Chesapeake Bay.

8. The method of claim 6, wherein the geographic strain of perch is selected from the Sassafras River.

9. The method of claim 1, wherein multiple generations of the perch are used to develop spawning cycles in all months of the year for a strain of perch.

10. The method of claim 1, wherein manipulating a spawning cycle of perch across multiple generations is performed on a commercial scale.

11. A method of manipulating a spawning cycle of perch comprising:
    selecting a strain of yellow perch from the Chesapeake Bay and manipulating at least one of temperature and photoperiod to shift the spawning cycle thereof from a natural spawning period to a first out-of-cycle spawning period to arrive at a first generation broodstock that spawns in the first out-of-cycle spawning period;
    dividing the first generation broodstock into a first group and a second group;
    developing a second generation broodstock from the first group within the first generation broodstock;
    manipulating the spawning period of the second generation broodstock to a second out-of-cycle spawning period using at least one of temperature and photoperiod manipulation; and
    developing at least one additional generation of broodstock from the second group within the first generation broodstock, wherein the additional generation of broodstock spawns during the first out-of-cycle spawning period.

12. The method of claim 11, wherein manipulating a spawning cycle of perch is performed on a commercial scale.

13. The method of claim 11, wherein the temperature is manipulated by:
    identifying a local temperature profile for the strain of yellow perch from the Chesapeake Bay;
    maintaining winter temperatures for about 100 to about 180 days;
    increasing temperature by about 1° C. every 2 to 4 days for spring, wherein spring lasts for about 56 to about 60 days;
    extending or reducing the length of the summer season to achieve the first out-of-cycle spawning period;
    decreasing temperature by about 1° C. every 2 to 4 days for autumn, wherein autumn lasts for about 42 to about 60 days.

14. The method of claim 11, wherein the photoperiod is manipulated by:
    identifying a local photoperiod profile for the strain of yellow perch from the Chesapeake Bay;
    following a regional seasonal cycle of sunrise and sunset times to correspond with the season;
    extending or reducing the length of the summer season to achieve the desired out-of-cycle spawning period.

15. A method of manipulating a spawning cycle of perch comprising:
    selecting a strain of yellow perch from the Sassafras River and manipulating at least one of temperature and photoperiod to shift the spawning cycle thereof from a natural spawning period to a first out-of-cycle spawning period to arrive at a first generation broodstock that spawns in the first out-of-cycle spawning period;
    dividing the first generation broodstock into a first group and a second group;
    developing a second generation broodstock from the first group within the first generation broodstock;
    manipulating the spawning period of the second generation broodstock to a second out-of-cycle spawning period using at least one of temperature and photoperiod manipulation; and
    developing at least one additional generation of broodstock from the second group within the first generation broodstock, wherein the additional generation of broodstock spawns during the first out-of-cycle spawning period.

16. The method of claim 15, wherein manipulating a spawning cycle of perch is performed on a commercial scale.

17. The method of claim 15, wherein the temperature is manipulated by:
    identifying a local temperature profile for the strain of yellow perch from the Sassafras River;
    maintaining winter temperatures for about 100 to about 180 days;
    increasing temperature by about 1° C. every 2 to 4 days for spring, wherein spring lasts for about 56 to about 60 days;
    extending or reducing the length of the summer season to achieve the first out-of-cycle spawning period;
    decreasing temperature by about 1° C. every 2 to 4 days for autumn, wherein autumn lasts for about 42 to 60 days.

18. The method of claim 15, wherein the photoperiod is manipulated by:
    identifying a local photoperiod profile for the strain of yellow perch from the Sassafras River;
    following a regional seasonal cycle of sunrise and sunset times to correspond with the season;
    extending or reducing the length of the summer season to achieve the first out-of-cycle spawning period.

* * * * *

UNITED STATES PATENT AND TRADEMARK OFFICE
CERTIFICATE OF CORRECTION

| | | |
|---|---|---|
| PATENT NO. | : 7,836,852 B2 | |
| APPLICATION NO. | : 11/951882 | |
| DATED | : November 23, 2010 | |
| INVENTOR(S) | : Frederick P. Binkowski | |

It is certified that error appears in the above-identified patent and that said Letters Patent is hereby corrected as shown below:

Column 32 Claim 14, line 8, the word "desired" should read --first--.

Signed and Sealed this
Third Day of May, 2011

David J. Kappos
*Director of the United States Patent and Trademark Office*